US009085523B2

(12) United States Patent
Obitsu et al.

(10) Patent No.: US 9,085,523 B2
(45) Date of Patent: Jul. 21, 2015

(54) COMPOUND FOR TREATING CARTILAGE DISORDERS

(75) Inventors: Tetsuo Obitsu, Osaka (JP); Kousuke Tani, Osaka (JP); Hikaru Sugihara, Osaka (JP); Akio Nishiura, Osaka (JP); Shinsei Fujimura, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 9 days.

(21) Appl. No.: 14/237,037

(22) PCT Filed: Aug. 3, 2012

(86) PCT No.: PCT/JP2012/069820
§ 371 (c)(1),
(2), (4) Date: Feb. 11, 2014

(87) PCT Pub. No.: WO2013/021935
PCT Pub. Date: Feb. 14, 2013

(65) Prior Publication Data
US 2014/0171388 A1 Jun. 19, 2014

(30) Foreign Application Priority Data

Aug. 5, 2011 (JP) .................................. 2011-172082

(51) Int. Cl.
| A01N 37/08 | (2006.01) |
| A61K 31/215 | (2006.01) |
| C07C 59/56 | (2006.01) |
| C07C 405/00 | (2006.01) |
| C07C 235/06 | (2006.01) |
| C07C 235/16 | (2006.01) |
| C07C 65/28 | (2006.01) |
| A61K 9/00 | (2006.01) |
| A61K 47/26 | (2006.01) |
| A61K 47/48 | (2006.01) |

(52) U.S. Cl.
CPC .............. *C07C 59/56* (2013.01); *A61K 9/0019* (2013.01); *A61K 47/26* (2013.01); *A61K 47/48969* (2013.01); *C07C 65/28* (2013.01); *C07C 235/06* (2013.01); *C07C 235/16* (2013.01); *C07C 405/00* (2013.01); *C07C 2101/04* (2013.01); *C07C 2101/08* (2013.01); *Y10T 428/2982* (2015.01)

(58) Field of Classification Search
None
See application file for complete search history.

(56) References Cited

U.S. PATENT DOCUMENTS

| 6,110,969 A | 8/2000 | Tani et al. |
| 6,576,785 B1 | 6/2003 | Tani et al. |
| 2003/0186939 A1 | 10/2003 | Tani et al. |
| 2007/0270489 A1 | 11/2007 | Toguchida |
| 2012/0316241 A1 | 12/2012 | Toguchida |

OTHER PUBLICATIONS

Tani et al. Bioorganic & Medicinal Chemistry (2002), vol. 10, pp. 1093-1106.*
International Search Report (PCT/ISA/210) dated Oct. 9, 2012 issued by the International Searching Authority in International Application No. PCT/JP2012/069820.

* cited by examiner

*Primary Examiner* — Patrick Lewis
(74) *Attorney, Agent, or Firm* — Sughrue Mion, PLLC

(57) ABSTRACT

The present invention provides a compound of which active |form| is represented by a formula (A). and which can be injected into a joint cavity which is an affected part of disorders and can be accumulated in the joint cavity to exert the pharmacological effect thereof in a sustained manner, for the purpose of ameliorating cartilage disorders without developing any side effect. A compound according to the present invention, which is represented by a formula (I):

(I)

(wherein all of symbols are as defined in the description), is a compound that can achieve the above-mentioned purpose. This compound does not exhibit any side effect on the cardiovascular system even when the compound is administered in an effective amount for exhibiting a cartilage regeneration activity, and is therefore extremely useful as a safe and effective preventive and/or therapeutic agent for cartilage disorders. Since a suspension produced using this compound can be injected without requiring the incision of the affected part, it can reduce the burden on patients, and is extremely useful as a medicinal agent.

9 Claims, 4 Drawing Sheets

COMPOUND FOR TREATING CARTILAGE DISORDERS

TECHNICAL FIELD

The present invention relates to a compound represented by a formula (I):

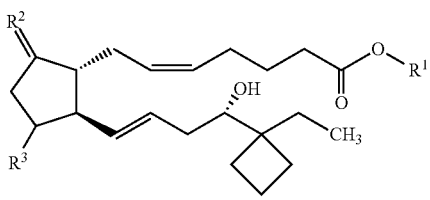

(wherein $R^1$, $R^2$ and $R^3$ have the same meanings as described later), a solvate thereof or a cyclodextrin clathrate thereof (hereinafter, may be referred to as a compound of the present invention) and a suspension manufactured by using the compound represented by formula (I).

BACKGROUND ART

Since articular cartilage is composed of hyaline cartilage lacking vascular, nerve and lymph, it is considered as a tissue that has very poor regeneration ability. Various factors such as genetic factor, injury and the like promote the release of proteoglycan from articular cartilage and at the same time, collagen type 2 which is fibrotic protein specifically existing in hyaline cartilage is decomposed. By these consecutive reaction, degeneration or destruction of articular cartilage tissue progresses irreversibly. As a result, an articulation loses smooth mobility and becomes difficult to absorb an external impact, which leads to cartilage disorder. In critical condition, an articulation loses the function itself. Aging is considered as one of the causes of cartilage disorder and the number of patients is expected to increase in a future aging society.

According to these circumstances, a compound which can achieve radical remedy of cartilage disorder is demanded. In addition, since the treatment of cartilage disorder takes long period, in view of reducing burden of patients, a medicine which can be directly injected to an affected part and exhibit sustained pharmacological efficacy is demanded. As a form that can be injected to the affected part and achieve sustained release the copolymer of lactic acid and glycol acid microsphere (PLGA-MS), liposome and the complex formulation with hyaluronic acid which is a component in articulation has been reported. However, PLGA-MS and liposome have safety concerns since there is possibility 1 of causing inflammation by infiltration of phagocyte or the like. In addition, regarding prior arts, any products which are retained in articulation for sufficient period and sustain a compound release have not been marketed and thus, a sustained release formulation technique for intra-articulation injection has not been established.

On the other hand, various prostaglandin derivatives are proposed as a novel medicine for radical remedy of cartilage disorder. For example, it is reported that a compound (refer to Patent Reference 1) represented by the formula (A):

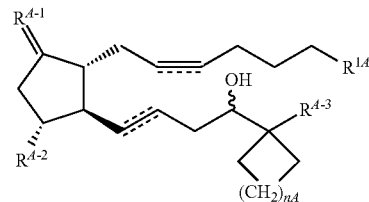

(wherein $R^{1,A}$ is carboxy or hydroxymethyl,
$R^{A-1}$ is oxo, methylene or halogen atom,
$R^{A-2}$ is hydrogen atom, hydroxy or C1-4 alkoxy,
$R^{A-3}$ is hydrogen atom, C1-8 alkyl, C2-8 alkenyl, C2-8 alkynyl
or
C1-8 alkyl, C2-8 alkenyl or C2-8 alkynyl substituted by 1 to 3 substituent (s) selected from the following (1) to (5) groups:
(1) halogen atom, (2) C1-4 alkoxy, (3) C3-7 cycloalkyl, (4) phenyl or (5) phenyl substituted by 1 to 3 substituent(s) selected from halogen atom, C1-4 alkyl, C1-4 alkoxyl, nitro and trifluoromethyl,
nA is 0 or integer from 1 to 4,
provided that (1) 5-6 position and 13-14 position are not triple bond at the same time (2) when 13-14 position is double bond, the double bond is E form, Z form or EZ mixture form is effective for cartilage injury (Patent Reference 2). In addition, it is disclosed that an implant formulation combining the compound represented by the formula (A) with hydrogel and biodegradable polymer is effective for cartilage related diseases (see Patent Reference 3).

However, in these references, there is no description or suggestion of the compound represented by formula (I) or a compound suitable for a formulation which is injectable into articular cavity.

PRIOR ART DOCUMENTS

Patent Reference

[Patent Reference 1] EP860430A
[Patent Reference 2] WO05/009468
[Patent Reference 3] JP-A-2007-099760

SUMMARY OF THE INVENTION

Problems to be Solved by the Invention

While the compound represented by formula (A) is effective for improving cartilage disorder, it is concerned that side effects of circulatory system such as decrease of blood pressure and increase of heart rates are brought by its EP2 agonist effect. Accordingly, the problem of the present invention is to provide a compound which improves cartilage disorder without causing these circulatory side effects, can be injected into articular cavity which is an affected part and of which active |form| is the compound represented by formula (A).

Means for Solving the Problems

The present inventors made studies to obtain formulation which is injectable into articular cavity which is an affected part, has excellent safety and releases its active form in a sustained manner in a topical site of articular for sufficient time. As a result, they found that, by esterifying the active form with long chain, the compound forms stable particles by itself. In addition, the present inventors found that when the particle diameter is as small as about 100 nm, the compound is transferred into blood without being retained inside articular cavity and cannot exhibit sufficient effect at an affected part or develops side effects. On the contrary, when the compound can form particles with a fixed particle diameter which is larger than 300 nm, the compound is able to be retained inside articular cavity for a long period. However, such particles agglutinate together and the particle diameter changes with time, thus it brought a new problem that the specific quality cannot be assured. In addition, there is also a problem that the particle does not release active forms inside articular for a sufficient time because the hydrolysis period varies depending on the structure of compound.

Therefore, the present inventors made further intensive study and found that the change of the particle size and diameter with time depends on an ester structure of the compound. Then, the present inventors found that the compound represented by formula (I) forms particle with appropriate size which meets the object of intra-articular injection and it is stable with time. In addition, the present inventors found that when the particle which the compound represented by formula (I) forms is injected into an affected part, it is retained in articular cavity for a long period and gradually hydrolyzed, and exhibits the pharmacological efficacy in a sustained manner. Further, the present inventors found that when the compound is administered even at the dose exhibiting the cartilage regeneration action, it does not develop circulatory side effects such as a decrease of blood pressure or an increase of heart rate, and thus completed the present invention.

Namely, the present invention relates to
1. A compound represented by a formula (I):

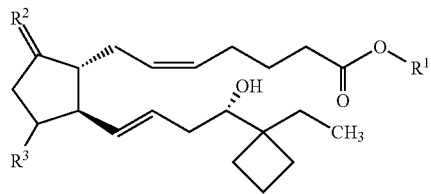

wherein $R^1$ is C10-22 alkyl, C10-22 alkenyl and C10-22 alkynyl,

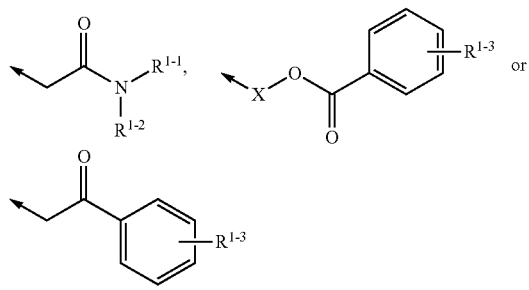

(an arrow of each group represents a bond position),
X is C2-4 alkylene;
$R^{1-1}$ is C10-20 alkyl optionally substituted by one phenyl, C10-20 alkenyl optionally substituted by one phenyl, C10-20 alkynyl optionally substituted by one phenyl, phenyl substituted by C10-20 alkyl, phenyl substituted by C10-20 alkenyl or phenyl substituted by C10-20 alkynyl;

$R^{1-2}$ is C1-3 alkyl or phenyl;
$R^{1-3}$ is C10-20 alkyl, C10-20 alkenyl, C10-20 alkynyl, C10-20 alkoxy, C10-20 alkenyloxy or C10-20 alkynyloxy;
$R^2$ is a hydrogen atom, hydroxy, oxo or a halogen atom;
$R^3$ is a hydrogen atom or hydroxy;

╌╌╌╌╌ represents a single bond or double bond;

⋰⋰⋰ represents binding to the opposite side of the sheet (namely α-configuration),

╱ represents binding to the front side of the sheet (namely β-configuration),

╱ represents that it is α-configuration, β-configuration or a mixture thereof at arbitrary ratio,
a solvate thereof or a cyclodextrin clathrate thereof,
2. The compound according to the above-mentioned 1, wherein $R^1$ is C12-22 alkenyl, C12-22 alkynyl or

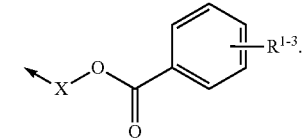

(all symbols in formula have the same meanings as described in above-mentioned 1),
3. The compound according to the above-mentioned 1, which is selected from a group consisting of 3-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}propyl 3-(pentadecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 3-(pentadecyloxy)benzoate, 4-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}butyl 3-(pentadecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 3-(dodecyloxy)benzoate, 2-{[(5Z)-7-{(1R,4R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 3-(tetradecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 3-(hexadecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 3-(octadecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 2-(pentadecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 4-(decyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 4-(dodecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 4-(tetradecyloxy)benzoate, 2-{[(5Z)-7-{(1R,2R,3R,5R)-5-chloro-2-[(1E,4S)-4-(1-ethylcyclobutyl)-4-hydroxy-1- buten-1-yl]-3-hydroxycyclopentyl}-5-heptenoyl]oxy}ethyl 4-(pentadecyloxy)benzoate, 3-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}propyl 4-(pentadecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 4-(hexadecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 4-(octadecyloxy)benzoate, (2R)-1-{[(5Z)-7-{(1R,2R,3R,5R)—S-chloro-2-[(1E,4S)-4-(1-ethylcyclobutyl)-4-hydroxy-1-buten-1-yl]-3-hydroxycyclopentyl}-5-heptenoyl]oxy}-2-propyl 4-(tetradecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 3-hexadecylbenzoate, 3-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}propyl 3-hexadecylbenzoate, 4-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}butyl 3-hexadecylbenzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 4-hexadecylbenzoate, 3-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}propyl 4-hexadecylbenzoate, 2-[methyl(4-pentadecylphenyl)amino]-2-oxoethyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-[methyl(15-phenylpentadecyl)amino]-2-oxoethyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-[methyl(tetradecyl)amino]-2-oxoethyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-[hexadecyl(methyl)amino]-2-oxoethyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-[methyl(octadecyl)amino]-2-oxoethyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-[icosyl(methyl)amino]-2-oxoethyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-[ethyl(octadecyl)amino]-2-oxoethyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-[octadecyl(phenyl)amino]-2-oxoethyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-octadecyn-yl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-pentadecyn-1-yl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-heptadecyn-1-yl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-nonadecyn-1-yl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-henicosyn-1-yl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, (2E)-2-hexadecen-1-yl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, (2E)-2-octadecen-1-yl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, (2E)-2-icosen-1-yl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, (2Z)-2-octadecen-1-yl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, undecyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, octadecyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, and 2-oxo-2-[2-(pentadecyloxy)phenyl]ethyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 4. A particle formed by a compound represented by formula (I), a solvate thereof or a cyclodextrin clathrate thereof, 5. The particle according to the above-mentioned 4, wherein the mean particle diameter is 0.5 to 5 μm.

6. A suspension which comprises a compound represented by formula (I), a solvate thereof or a cyclodextrin clathrate thereof, and as a dispersion medium, one or more kind selected from glucose solution, maltose solution, sucrose solution, lactose solution, trehalose solution, mannitol solution, maltitol solution, xylitol solution, dextran, distilled water for injection and saline, and also may comprise surfactant, 7. An agent for the prevention and/or treatment of cartilage disorder, comprising a compound represented by formula (I), a solvate thereof or a cyclodextrin clathrate thereof, 8. A method of the prevention and/or treatment of cartilage disorder, which comprises administering a compound represented by formula (I), a solvate thereof or a cyclodextrin clathrate thereof to a mammal, 9. Use of a compound represented by formula (I), a solvate thereof or a cyclodextrin clathrate thereof for the manufacture of a medicament for the prevention and/or treatment of cartilage disorder, and 10. A compound represented by formula (I), a solvate thereof or a cyclodextrin clathrate thereof for preventing and/or treating cartilage disorder, The Effect of the Invention The compound of the present invention, to improve cartilage disorder, can be injected into articular cavity which is an affected part and exhibit pharmacological efficacy in a sustained manner by being retained in articular cavity. The compound of the present invention has an excellent cartilage regeneration effect and does not develop circulatory side effects when an even sufficient amount exhibiting cartilage regeneration action is administered, thus, it is useful as a treating agent for cartilage disorder such as cartilage injury, articular disk injury, meniscal injury, osteochondral defect, osteoarthritis and the like.

MODE FOR CARRYING OUT THE INVENTION

Figure 1:
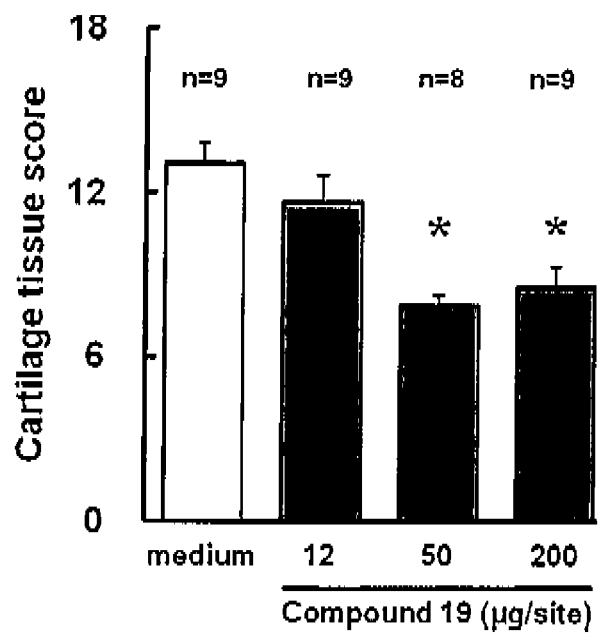
FIG. 1 shows the action of Compound 19 in knee cartilage defect model (*$p<0.05$ vs vehicle: Steel test).

The present invention relates to a compound represented by formula (I):

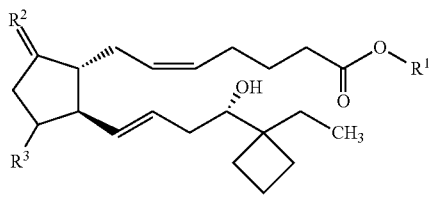

wherein $R^1$ is C10-22 alkyl, C10-22 alkenyl and C10-22 alkynyl,

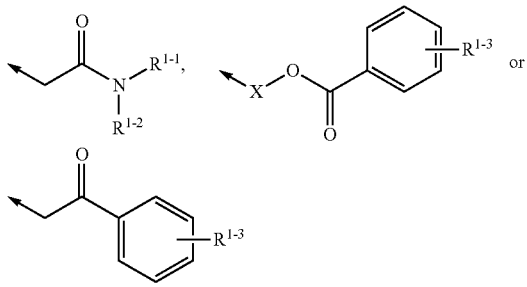

(an arrow of each group represents a bond position),
X is C2-4 alkylene;
$R^{1-1}$ is C10-20 alkyl optionally substituted by phenyl, C10-20 alkenyl optionally substituted by phenyl, C10-20 alkynyl optionally substituted by phenyl, phenyl substituted by C10-20 alkyl, phenyl substituted by C10-20 alkenyl or phenyl substituted by C10-20 alkynyl;
$R^{1-2}$ is C1-3 alkyl or phenyl;
$R^{1-3}$ is C10-20 alkyl, C10-20 alkenyl, C10-20 alkynyl, C10-20 alkoxy, C10-20 alkenyloxy or 010-20 alkynyloxy;
$R^2$ is a hydrogen atom, hydroxy, oxo or a halogen atom;
$R^3$ is a hydrogen atom or hydroxy;
------- represents single bond or double bond;
,,,,\\\ represents binding to the opposite side of the sheet (namely α-configuration),
◢ represents binding to the front side of the sheet (namely β-configuration),
◢ represents that it is α-configuration, β-configuration or a mixture thereof at arbitrary ratio, a solvate thereof or a cyclodextrin clathrate thereof (hereinafter the compound represented by the formula (I), the solvate thereof or the cyclodextrin clathrate thereof may be referred as a compound of the present invention).

In the specification, C10-22 alkyl refers to decyl, undecyl, dodecyl, tridecyl, tetradecyl, pentadecyl, hexadecyl, heptadecyl, ocatdecyl, nonadecyl, icosyl, henicosanyl, docosanyl and isomers thereof.

In the specification, C10-22 alkenyl refers to decenyl, undecenyl, dodecenyl, tridecenyl, tetradecenyl, pentadecenyl, hexadecenyl, heptadecenyl, octadecenyl, nonadecenyl, icosenyl, henicosenyl, docosenyl, decadienyl, undecadienyl, dodecadiynyl, tridecadienyl, tetradecadienyl, pentadecadienyl, hexadecadiynyl, heptadecadienyl, octadecadienyl, nonadecadienyl, icosadienyl, henicosadienyl, docosadienyl, decatrienyl, undecatrienyl, dodecatrienyl, tridecatrienyl, tetradecatrienyl, pentadecatrienyl, hexadecatrienyl, heptadecatrienyl, octadecatriynyl, nonadecatrienyl, icosatrienyl, henicosatrienyl, docosatrienyl and isomers thereof.

In the specification, C10-22 alkynyl refers to decynyl, undecynyl, dodecynyl, tridecynyl, tetradecynyl, pentadecynyl, hexadecynyl, heptadecynyl, octadecynyl, nonadecynyl, icosynyl, henicosynyl, docosynyl, decadiynyl, undecadiynyl, dodecadiynyl, tridecadiynyl, tetradecadiynyl, pentadecadiynyl, hexadecadiynyl, heptadecadiynyl, octadecadiynyl, nonadecadiynyl, icosadiynyl, henicosadiynyl, docosadiynyl, decatriynyl, undecatriynyl, dodecatriynyl, tridecatriynyl, tetradecatriynyl, pentadecatriynyl, hexadecatriynyl, heptadecatriynyl, octadecatriynyl, nonadecatriynyl, icosatriynyl, henicosatriynyl, docosatriynyl and isomers thereof.

In the specification, C10-20 alkyl refers to decyl, undecyl, dodecyl, tridecyl, tetradecyl, pentadecyl, hexadecyl, heptadecyl, ocatdecyl, nonadecyl, icocyl and isomers thereof.

In the specification, C10-20 alkenyl refers to decenyl, undecenyl, dodecenyl, tridecenyl, tetradecenyl, pentadecenyl, hexadecenyl, heptadecenyl, octadecenyl, nonadecenyl, icosenyl, decadienyl, undecadienyl, dodecadiynyl, tridecadienyl, tetradecadienyl, pentadecadienyl, hexadecadienyl, heptadecadienyl, octadecadienyl, nonadecadienyl, icosadienyl, decatrienyl, undecatrienyl, dodecatrienyl, tridecatrienyl, tetradecatrienyl, pentadecatrienyl, hexadecatrienyl, heptadecatrienyl, octadecatrienyl, nonadecatrienyl, icosatrienyl and isomers thereof.

In the specification, C10-20 alkynyl refers to decynyl, undecynyl, dodecynyl, tridecynyl, tetradecynyl, pentadecynyl, hexadecynyl, heptadecynyl, octadecynyl, nonadecynyl, icosynyl, decadiynyl, undecadiynyl, dodecadiynyl, tridecadiynyl, tetradecadiynyl, pentadecadiynyl, hexadecadiynyl, heptadecadiynyl, octadecadiynyl, nonadecadiynyl, icosadiynyl, decatriynyl, undecatriynyl, dodecatriynyl, tridecatriynyl, tetradecatriynyl, pentadecatriynyl, hexadecatriynyl, heptadecatriynyl, octadecatriynyl, nonadecatriynyl, icosatriynyl and isomers thereof.

In the specification, C1-3 alkyl refers to methyl, ethyl, propyl and isopropyl.

In the specification, C10-20 alkoxy refers to decyloxy, undecyloxy, dodecyloxy, tridecyloxy, tetradecyloxy, pentadecyloxy, hexadecyloxy, heptadecyloxy, octadecyloxy, nonadecyloxy, icosyloxy and isomers thereof.

In the specification, C10-20 alkenyloxy refers to decynyloxy, undecenyloxy, dodecenyloxy, tridecenyloxy, tetradecenyloxy, pentadecenyloxy, hexadecenyloxy, heptadecenyloxy, octadecynyloxy, nonadecenyloxy, icosenyloxy, decadienyloxy, undecadienyloxy, dodecadienyloxy, tridecadienyloxy, tetradecadienyloxy, pentadecadiynyloxy, hexadecadienyloxy, heptadecadienyloxy, octadecadiynyloxy, nonadecadienyloxy, icosadienyloxy, decatrienyloxy, undecatrienyloxy, dodecatriynyloxy, tridecatriynyloxy, tetradecatriynyloxy, pentadecatriynyloxy, hexadecatriynyloxy, heptadecatrienyloxy, octadecatrienyloxy, nonadecatrienyloxy, icosatrienyloxy and isomers thereof.

In the specification, C10-20 alkynyloxy refers to decynyloxy, undecynyloxy, dodecynyloxy, tridecynyloxy, tetradecynyloxy, pentadecynyloxy, hexadecynyloxy, heptadecynyloxy, octadecynyloxy, nonadecynyloxy, icosynyloxy, decadiynyloxy, undecadiynyloxy, dodecadiynyloxy, tridecadiynyloxy, tetradecadiynyloxy, pentadecadiynyloxy, hexadecadiynyloxy, heptadecadiynyloxy, octadecadiynyloxy, nonadecadiynyloxy, icosadiynyloxy, decatriynyloxy, undecatriynyloxy, dodecatriynyloxy, tridecatriynyloxy, tetradecatriynyloxy, pentadecatriynyloxy, hexadecatriynyloxy, heptadecatriynyloxy, octadecatriynyloxy, nonadecatriynyloxy, icosatriynyloxy and isomers thereof.

In the specification, C2-4 alkylene refers to ethylene, propylene, butylene and isomers thereof.

In the specification, a halogen atom refers to fluorine, bromine, chlorine, iodine and the like.

In compounds represented by formula (I), the compound represented by formula (I-1)

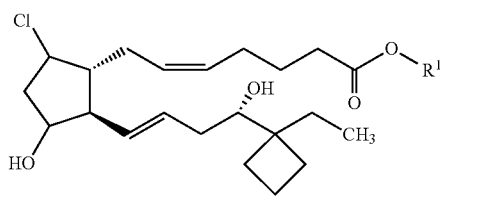
(I-1)

wherein $R^1$ have the same meaning as described above is preferable.

In formula (I) or (I-1), it is preferable that $R^1$ is C12-22 alkenyl, C12-22 alkynyl or

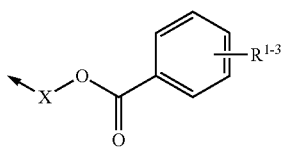

wherein and X have the same meaning as described above; it is more preferable that $R^1$ is C15-20 alkenyl, C15-20 alkynyl,

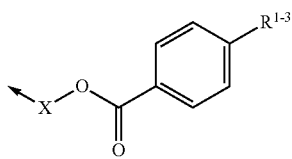

wherein $R^{1-3}$ and X have the same meaning as described above
or

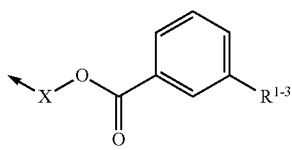

wherein $R^{1-3}$ and X have the same meanings as described above.

It is preferable that $R^2$ is a halogen atom.
It is preferable that $R^3$ is hydroxy.
Further, all compounds described in Examples are preferable.

Unless otherwise specified, all isomers are included in the present invention. For example, alkyl, alkenyl, alkynyl and alkoxy include straight and branched isomers. Further, isomers based on double bond, ring, fused ring (E, Z, cis, trans), isomers obtained from the presence of asymmetric carbon(s) (R-configuration, S-configuration, α-configuration, β-configuration, enantiomers, diastereoisomers), optically active compounds having optical rotation (D, L, d, l-configuration), polar compounds obtained by chromatographic separations (highly polar compound, less polar compound), equilibrium compounds, rotational isomers, mixtures of them at an arbitrary ratio and racemic mixtures are all included in the present invention.

Examples of suitable solvates of the compound represented by formula (I) include solvate of water and solvates of alcoholic solvents (e.g., ethanol). It is preferable that these solvates are nontoxic and water soluble.

The compound of the present invention can be converted into a cyclodextrin clathrate by the methods described in the descriptions of JP-A-50-3362, JP-A-52-31404 or JP-A-61-52146 using α-β- or γ-cyclodextrin or a mixture thereof. Since converting into a cyclodextrin clathrate increases its stability, it is preferable to use as medicament. Whether the compound of the present invention is included in cyclodextrin can be confirmed with the result of differential scanning calory measurement or powder X-ray diffraction test.

The compound of the present invention forms particle by being dropped into agitated dispersion medium such as glucose solution, maltose solution and the like with or without surfactant. When the particle is injected inside articular cavity, in case where the particle size is too small, it is not retained inside articular cavity for sufficient time and transferred into systemic circulation. In case where the particle size is too large, its sedimentation velocity gets large and the quality control becomes difficult. Therefore, as a particle prepared with the compound of the present invention, a particle with a mean particle diameter which enables the particle retained inside articular cavity and maintains a stable diameter is preferable. Concretely, a particle with the mean particle diameter of about from 0.5 μm to 5 μm is preferable.

In the specification, the mean particle diameter means the mean particle diameter measured by a laser diffraction/scattering method. In the specification, the mean particle diameter is measured by a laser diffraction grain size distribution measuring apparatus (SALD-2100: manufactured by Shimadzu Corp.). In terms of mean particle diameter, various values such as volume mean diameter, surface mean diameter, median diameter and the like are used as an indicator of mean particle diameter, and in the specification, volume mean diameter (Dv) is used as a mean particle diameter.

In addition, a particle to be injected inside articular cavity is preferably a particle with a mean particle diameter with less variance and uniform size. The variance of mean particle diameter can be evaluated by measuring particle size distribution and the particle size distribution can be measured by a laser diffraction grain size distribution measuring apparatus as well as a mean particle diameter. PDI (Poly Dispersity Index) value=Dv/Dn (number mean particle diameter) is used as an indicator of particle size distribution. As a particle formed by the compound of the present invention, the PDI value is preferably 4 or less. In the description, PDI value and Dn was measured by a laser diffraction grain size distribution measuring apparatus (SALD-2100: manufactured by Shimadzu Corp.).

Processes for the Preparation of the Compound of the Present Invention

The compound of the present invention can be prepared by improving or combining appropriately the known methods described in the description of EP860430A or Synlett 2002, No. 1, 239-242 or Comprehensive Organic Transformations A Guide to Functional Group Preparations, 2nd Edition (Richard C. Larock, John Wiley & Sons Inc, 1999), the methods described following, or the methods described in Examples and the like.

The compound represented by the formula (I) can be prepared by treating with the following esterification of the carboxylic acid derivative represented by formula (II):

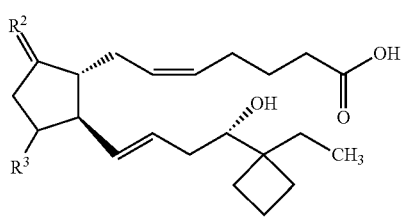

(all symbols in the formulation have the same meanings as described above) and the compound represented by formula (III)

wherein Q is a leaving group (halogen atom, tosyloxy, mesyloxy, trifluoromethanesulfonyloxy, nosyloxy and the like) and $R^1$ has the same meaning as described above.

The esterification is known. For example, the compound represented by formula (I) can be prepared by reaction of the carboxylic acid derivative represented by formula (II) and the compound represented by formula (III) in an organic solvent (e.g., dimethylfolmamide, dimethylacetamide, dimethyl imidazolidinone, tetrahydrofuran, diethylether, dichloromethane, chloroform and the like) in the presence of base (e.g., potassium carbonate, sodium carbonate, cesium carbonate, sodium hydride, t-butoxypotassium, sodium methoxide, sodium ethoxide and the like) at 0 to 100° C.

The above esterification can be carried out either in the presence or absence of inert gas such as argon or nitrogen.

The compound represented by formula (I) can be prepared by treating with the following esterification of the carboxylic acid derivative of formula (II) and the alcohol represented by formula (IV)

($R^1$ has the same meaning as described above).

The esterification is known. For example, it includes (1) dehydration-condensation reaction in the presence of acid catalyst, (2) ester exchange reaction, etc.

(1) Dehydration-condensation reaction in the presence of acid catalyst

The compound represented by formula (I) can be prepared, for example, by reaction of the carboxylic acid derivative represented by formula (II) in an organic solvent (the alcohol represented by formula (IV) or a mixed solvent of the said alcohol and other organic solvents), in the presence of acid (an inorganic acid (e.g., sulfuric acid, hydrochloric acid and the like), an organic acid (e.g., p-toluene sulfuric acid, trifluoro acetic acid and the like) or Lewis acid (e.g., boron trifluoride diethylether complex and the like)) at 0 to 100° C.

(2) Ester exchange reaction

The compound represented by formula (I) can be prepared, for example, by reaction of the simple ester such as methylester of the carboxylic acid derivative represented by formula (II) in alcohol solvent represented by formula (IV), in the presence of acid (an inorganic acid (e.g., sulfuric acid, hydrochloric acid and the like), an organic acid (e.g., p-toluene sulfonic acid, trifluoro acetic acid and the like) or Lewis acid (e.g., boron trifluoride diethylether complex and the like)), base (e.g., potassium carbonate, sodium carbonate, cesium carbonate, t-butoxy potassium, sodium methoxide, sodium ethoxide and the like) or titanium alkoxide (e.g., titanium tetraisopropoxide and the like) at 0 to 100° C.

In addition to the above esterification, the following esterifications such as (3) the method using an acyl halide, (4) the method using a mixed acid anhydride and (5) the method using a condensing agent may be used.

These methods are explained concretely below.

(3) The method using an acyl halide may be carried out, for example, by reacting carboxylic acid with an acyl halide (e.g., oxalylchloride, thionylchloride and the like) in an organic solvent (e.g., chloroform, dichloromethane, diethylether, tetrahydrofuran and the like) or without a solvent at −20° C. to reflux temperature, and then the obtained acyl halide derivative is reacted with alcohol in an organic solvent (e.g., chloroform, dichloromethane, diethylether, tetrahydrofuran and the like) in the presence of a base (e.g., pyridine, triethylamine, dimethylaniline, dimethylaminopyridine, diisopropylethylamine and the like) at 0 to 40° C. Alternatively, the obtained acyl halide derivative may be reacted in an organic solvent (e.g., dioxane, tetrahydrofuran and the like) using an alkaline aqueous solution (e.g. sodium bicarbonate, sodium hydroxide and the like) at 0 to 40° C.

(4) The method using a mixed acid anhydride may be carried out, for example, by reacting carboxylic acid with an acyl halide (e.g., pivaloyl chloride, tosyl chloride, mesyl chloride and the like) or an acid derivative (e.g., ethyl chloroformate, isobutyl chlorofonnate and the like) in an organic solvent (e.g. chloroform, dichloromethane, diethyl ether, tetrahydrofuran and the like) or without a solvent, in the presence of a base (e.g., pyridine, triethylamine, dimethylaniline, dimethylaminopyridine, diisopropylethylamine and the like) at 0 to 40° C., and then the obtained mixed acid anhydride derivative may be reacted with alcohol in an organic solvent (e.g., chloroform, dichloromethane, diethyleher, tetrahydrofuran and the like), at 0 to 40° C.

(5) The method using a condensing agent may be carried out, for example, by reacting carboxylic acid with alcohol in an organic solvent (e.g., chloroform, dichloromethane, dimethylformamide, diethyl ether, tetrahydrofuran and the like) or without a solvent, in the presence or absence of a base (e.g., pyridine, triethylamine, dimethylaniline, dimethylaminopyridine and the like), using a condensing agent (e.g., 1,3-dicyclohexyl carbodiimide (DCC), 1-ethyl-3-[3-(dimethyl amino)propyl]carbodiimide (EDC), 1,1'-carbodiimidazole (CDI), 2-chloro-1-methylpyridinium iodide or 1-propanephosphonic acid cyclic anhydride (PPA) and the like), in the presence or absence of 1-hydroxybenzotriazole (HOBO at 0 to 40° C.

In the above preparation processes, the compound represented by formula (II) can be prepared by the methods described in the description of EP860430A or the partially modified methods thereof.

The compound represented by formula (IV) and the other test compounds are known or can be prepared easily by the combination of the known methods such as the methods described in *Comprehensive Organic Transformations: A Guide to Functional Group Preparations,* 2nd Edition (Richard C. Larock, John Wiley & Sons Inc, 1999) or Elmer J. Rauckman et, al., *J. Org. Chem.*, vol. 41, No. 3, 1976, p564-565 and the like.

In each reaction of the specification, the reactions with heating, as will be apparent to those skilled in the art, it may be carried with water bath, oil bath, sand bath and microwave.

In each reaction of the specification, it may be used a solid phase reagent which is supported by polymer (for example, polystyrene, polyacrylamide, polypropylene, polyethyleneglycol and the like).

In each reaction of the specification, the obtained products may be purified by conventional techniques. For example, the purification may be carried out by distillation at atmospheric or reduced pressure, by high performance liquid chromatography with silica gel or magnesium silicate, by thin layer chromatography, by ion exchange resin, by scavenger resin, by column chromatography, by washing or by recrystallization. The purification may be carried out at each reaction or after several reactions.

Toxicity

The side effect of the compound of the present invention is very low and therefore the compound is considered safe for pharmaceutical use.

Application to Pharmaceuticals

Since the compound of the present invention has cartilage regeneration action, it can be used for the objective of the prevention and/or treatment of cartilage disorder, such as cartilage damage, articular disk damage, menisci injury, osteochondral defect and osteoarthritis (e.g., gonarthrosis, coxarthrosis and the like), rheumatoid arthritis, osteoporosis, periarthritis scapulohumeralis, chondrodysplasia, achondroplasia, achondroplasia, bone deformation or spondylosis deformans, dyschondrogenesis, chondrodystrophia, articular chondrocalcinosis, acute purulent arthritis, tuberculous arthritis, syphilitic arthritis, systemic lupus erythematosus, disk herniation, keypuncher's disease, osteosarcoma, myeloma, osteomalacia, rickets, osteitis fibrosa, renal ostaodystrophy, bone Behcet disease, relapsing polychondritis, arthritis of the temporomandibular joint, cartilage defect, osteochondritis dissecans, articular cartilage damage by injury, anotia, microtia. In addition, the cartilage regeneration action of the compound of the present invention can be utilized to promote callus formation in the process of fracture repair. Therefore, since the compound of the present invention is, for example, expected to promote fracture repair and improve fracture repair failure, it can be used for the promotion of fracture repair and treatment of fracture repair failure. Further, the compound of the present invention can be used for the objective of surgical treatment of cartilage disorder, for example, bone fenestration, osteochondral graft, cartilage cell transplantation and debridement, and also for a culture of cell cartilage for transplantation or a transplantation of the cell. In addition, the compound of the present invention can be administered with cartilage cell for transplantation.

The compound of the present invention may be administered by combining with other surgical treatments and/or medicines as a combined preparation, for 1) supplementing and/or enhancing of therapeutic effect of cartilage disorder, 2) improvement in pharmacokinetics and absorption and reduction of dose of the compound, and/or 3) reduction of side effect of the compound.

In case of administering the compound of the present invention combined with surgical treatment, it may be administered simultaneously or at different times. In the case of administration at different times, the time after the surgical treatment is not particularly limited.

The compound of the present invention and other medicaments may be administered in the form of combination preparation having these components incorporated in one preparation or may be administered in separate preparations. In the case where these medicaments are administered in separate preparations, they may be administered simultaneously or at different times. In the administration at different times, the medicament of the present invention may be administered in advance and the other medicaments may be administered later. Alternatively, the other medicaments may be administered in advance and the medicament of the present invention may be administered later. The administration route of the other medicaments is not particularly limited and it may be either oral or parenteral administration.

The other medicaments may be low-molecular compounds. In addition, they may be macromolecular protein, polypeptide, polynucleotide (DNA, RNA, and gene), antisense, decoy, antibody or vaccine and so on. The dose of the other medicaments can be accordingly selected as a standard of clinical dose. Additionally, the compounding ratio of the compound of the present invention and the other medicaments can be accordingly selected by the age and body weight of object to be administered, the administration method, the administration time and the like. For example, the other medicaments may be used from 0.01 to 100 parts by weight relative to 1 part by weight of the medicament of the present invention. The medicaments may be administered by combining arbitrary two or more kinds at an appropriate proportion. The other medicaments to compensate for and/or enhance the therapeutic effect of the compound of the present invention do not only include ones which have ever been found but ones which will be found from now based on the above-mentioned mechanism.

The compound of the present invention can be administered in combination with other medicaments, for example bone morphogenetic protein (BMP), steroid, nonsteroidal anti-inflammatory drug, hyaluronic acid drug, prostaglandins, growth factors, vitamin D derivative, vitamin A derivative, metalloproteinase inhibitor, phosphodiesterase 4 (PDE4) inhibitor, elastase inhibitor, glycosaminoglycan drug, NFκB decoy oligo and the like. The compounding ratio of the compound of the present invention and the other medicaments is not particularly limited. The other medicaments may be administered by combining arbitrary same kind or different two or more kinds.

The other medicaments to compensate for and/or enhance the therapeutic effect of the compound of the present invention do not only include ones which have ever been found but ones which will be found from now based on the above-mentioned mechanism.

In order to use the compound of the present invention for above purposes, usually, it is locally administered in a parenteral form. A dose is different depending on an age, a weight, symptom, therapeutic effect, an administration method, a treatment time and the like, but usually, the compound of the present invention is injected at an affected part in a range of 1 ng to 100 mg per once per adult, once a day to two months. Of course, as described above, since a dose varies depending on a variety of conditions, the dose is sufficient at a dose smaller than the aforementioned dose in some cases, or administration beyond the range is required in some cases.

Injectables for parenteral administration include suspensions, emulsions and solid injectables which are used by suspending in a dispersion medium upon use. Injectables are used by suspending or emulsifying one or more active substances in a suspending media. As the dispersion medium to suspend or emulsify the compound of the present invention, for example, a solution of sugar alcohol such as glucose solution, maltose solution, sucrose solution, lactose solution, trehalose solution, mannitol solution, maltitol solution, xylitol solution and the like, polysaccharide such as dextran and the like, distilled water for injection, saline and a combination of them are used. Further, the injectables may contain surfactants (e.g., Polysorbate 80 (registered trademark) etc.), stabilizers, suspending agents, emulsifiers, soothing agents, buffers or preservatives and the like. These are produced by sterilization or a sterile operation method at a final step. Alternatively, injectables can be also used as aseptic solid agents (e.g. lyophilized products are produced, and dissolved in distilled water for injection or other solvent which has been sterilized or are aseptic, before use thereof). It is preferable that the injectables to inject the compound of the present invention at an affected part is suspension which comprises the compound of the present invention, also may comprise surfactants. In addition, it is preferable that the dispersion medium to suspend the compound of the present invention is glucose solution or maltose solution.

EXAMPLES

Although the following describes the present invention in detail with examples, the present invention is not limited hereto.

A solvent in parenthesis shown at places of separation by chromatography and in TLC indicates an elution solvent or a development solvent used, and a proportion indicates a volumetric ratio.

Unless otherwise specified, NMR data is $^1$H-NMR data in 300 MHz.

The solvents in parenthesis in NMR show the solvents used for measurement.

The compounds used herein were named by a computer program which names chemical names according to the IUPAC rules, ACD/Name Batch (registered trademark), or according to IUPAC nomenclature. For example, solution, it was diluted with ethyl acetate and filtered through Celite (brand name). The filtrate was concentrated under reduced pressure and the residue was purified by silica gel column chromatography (hexane:ethyl acetate=9:1→4:2) to obtain the title compound (6.3 g) having the following physical property values.

TLC: Rf 0.75 (hexane:ethyl acetate=8:2);
$^1$H-NMR (CDCl$_3$): δ 0.88 (t, J=6.9 Hz, 3H), 1.15-1.63 (m, 24H), 1.70-1.85 (m, 2H), 3.91 (s, 3H), 3.99 (t, J=6.6 Hz, 2H), 7.08 (ddd, J=7.8, 2.4, 0.9 Hz, 1H), 7.32 (t, J=7.8 Hz, 1H), 7.53 (dd, 1.5 Hz, 1H), 7.60 (ddd, J=7.8, 1.5, 0.9 Hz, 1H), Example 2

3-(pentadecyloxy)benzoic acid (Compound 2)

Compound 1 (2.0 g) was dissolved in tetrahydrofuran (9.0 mL) and ethanol (9.0 mL). Thereto, 5 N aqueous sodium hydroxide solution (2.2 mL) was added, followed by stirring at 70° C. for 14 hours. To the reaction solution, 5 N hydrochloric acid (2.2 mL) and water (18 mL) were added and cooled to 40° C. The obtained solid was filtered and dried under reduced pressure to obtain the title compound (1.9 g) having the following physical property values.

TLC: Rf 0.45 (hexane:ethyl acetate=6:4);
$^1$H-NMR (CDCl$_3$): δ 0.88 (t, J=6.9 Hz, 3H), 1.15-1.53 (m, 24H), 1.70-1.85 (m, 2H), 4.01 (t, J=6.6 Hz, 2H), 7.13 (ddd, J=8.1, 2.4, 0.9 Hz, 1H), 7.36 (t, J=7.8 Hz, 1H), 7.59 (m, 1H), 7.68 (dt, J=7.8, 0.9 Hz, 1H).

Example 3

3-bromopropyl 3-(pentadecyloxy)benzoate (Compound 3)

Compound 2 (300 mg) was dissolved in 1,2-dichloroethane (2.5 mL). Thionyl chloride (0.15 mL) and dimethylformamide (one drop) were added thereto, followed by stirring at 50° C. for 20 hours. The reaction solution was concentrated under reduced pressure. To the obtained residue was added

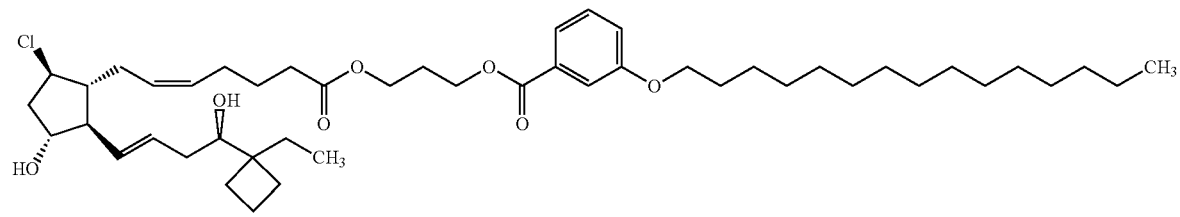 [SMILES: CCCCCCCCCCCCCCCOc1cccc(C(=O)OCCCOC(=O)CCC/C=C\C[C@@H]2[C@@H](/C=C/C[C@@H](O)C3(CC)CCC3)[C@H](O)C[C@H]2Cl)c1]

was named as 3-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}propyl 3-(pentadecyloxy)benzoate, Preparation Examples Example 1 methyl 3-(pentadecyloxy)benzoate (Compound 1)

Methyl 3-hydroxy benzoate (2.7 g) was dissolved in acetonitrile (30 mL) and potassium carbonate (4.8 g) and 1-bromopentadecane (5.1 g) were added thereto, followed by stirring at 60° C. for 7 hours. After cooling of the reaction 1,2-dichloroethane (9.0 mL), and the residue was dissolved. The solution was carefully added to the solution of 3-bromo-1-propanol (0.15 mL) in pyridine (0.35 mL) at room temperature, followed by stirring for 2.5 hours. To the reaction solution, water was added, followed by extraction with dichloromethane. The organic layer was washed with water and an aqueous saturated sodium chloride solution, dried with anhydrous magnesium sulfate, and concentrated under reduced pressure. The obtained residue was purified by silica gel column chromatography (hexane:ethyl acetate=99:1→95:5) to obtain the title compound (240 mg) having the following physical property values.

TLC: Rf 0.72 (hexane:ethyl acetate=8:2);
$^1$H-NMR (CDCl$_3$): δ 0.88 (t, J=6.9 Hz, 3H), 1.15-1.55 (m, 26H), 232 (m, 2H), 3.54 (t, J=6.6 Hz, 2H), 3.99 (t, J=6.6 Hz, 2H), 4.46 (t, J=6.3 Hz, 2H), 7.08 (m, 1H), 7.32 (t, 7=8.1 Hz, 1H), 7.53 (m, 1H), 7.59 (m, 1H).

Example 4

3-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}propyl 3-(pentadecyloxy)benzoate (Compound 4)

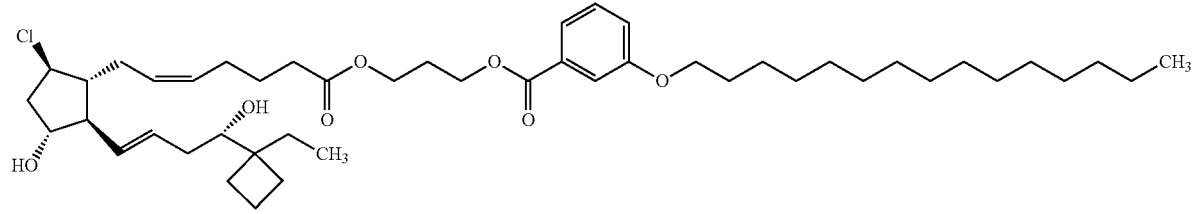 [SMILES: CCCCCCCCCCCCCCCOc1cccc(C(=O)OCCCOC(=O)CCC/C=C\C[C@@H]2[C@@H](/C=C/C[C@H](O)C3(CC)CCC3)[C@H](O)C[C@H]2Cl)c1]

Compound A (210 mg) was dissolved in N-methylpyrrolidone (3.0 mL) and Compound 3 (240 mg), potassium carbonate (110 mg) and sodium iodide (15 mg) were added thereto, followed by stirring at 50° C. for 2 hours. After cooling the reaction solution, hexane (2.5 mL) and ethyl acetate (2.5 mL) were added thereto, and the solution was poured into water, followed by extraction with ethyl acetate. The organic layer was washed with water and aqueous saturated sodium chloride, dried with anhydrous magnesium sulfate, and concentrated under reduced pressure. The obtained residue was purified by silica gel column chromatography (hexane:ethyl acetate=90:10→60:40) to obtain the title compound (340 mg) having the following physical property values.

TLC: Rf 0.42 (hexane:ethyl acetate=6:4);
$^1$H-NMR (CDCl$_3$): δ 0.88 (t, 0.1-7.2 Hz, 3H), 0.91 (t, J=7.5 Hz, 3H), 1.16-2.36 (m, 52H), 3.52 (m, 1H), 3.94-4.16 (m, 4H), 4.24 (t, J=6.0 Hz, 2H), 4.39 (t, J=6.3 Hz, 2H), 5.35-5.65 (m, 4H), 7.08 (dd, J=7.8, 2.7 Hz, 1H), 7.32 (t, J=7.8 Hz, 1H), 7.52 (m, 1H), 7.59 (d, J=7.5 Hz, 1H);
MASS: (FAB, Pos.) 787 (M+H)$^+$.

Example 4 (1)-(15)

By the same procedure as a series of reactions of Example 1→Example 2→Example 3→Example 4 using methyl 3-hydroxybenzoate or a corresponding substituted benzoic acid ester, and 1-bromopentadecane or a corresponding compound, and 3-bromo-1-propanol or a corresponding alcohol, the following compounds were obtained.

Example 4 (1)

2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 3-(pentadecyloxy)benzoate (Compound 4-1)

TLC: Rf 0.44 (hexane:ethyl acetate=6:4);
$^1$H-NMR (CDCl$_3$): δ 0.88 (t, J=6.9 Hz, 3H), 0.91 (t, J=7.5 Hz, 3H), 1.20-2.32 (m, 48H), 2.36 (t, J=7.5 Hz, 2H), 3.53 (m, 1H), 3.93-4.15 (m, 4H), 4.37-4.45 (m, 2H), 4.47-4.54 (m, 2H), 5.35-5.50 (m, 3H), 5.52-5.65 (m, 1H), 7.10 (m, 1H), 7.33 (t, J=7.8 Hz, 1H), 7.54 (m, 1H), 7.61 (m, 1H).
MASS: (FAB, Pos.) 773 (M+H)$^+$

Example 4 (2)

4-{([(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}butyl 3-(pentadecyloxy)benzoate (Compound 4-2)

TLC: Rf 0.47 (hexane:ethyl acetate=6:4);
$^1$H-NMR (CDCl$_3$): δ 0.88 (t, J=7.2 Hz, 3H), 0.91 (t, J=7.5 Hz, 3H), 1.16-2.35 (m, 54H), 3.52 (m, 1H), 3.94-4.18 (m, 6H), 4.34 (t, J=6.0 Hz, 2H), 5.35-5.65 (m, 4H), 7.08 (m, 1H), 7.32 (t, J=7.8 Hz, 1H), 7.53 (m, 1H), 7.59 (d, J=7.8 Hz, 1H);
MASS: (FAB, Pos.) 801 (M+H)$^+$

Example 4 (3)

2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 3-(dodecyloxy)benzoate (Compound 4-3)

TLC: Rf 0.47 (hexane:ethyl acetate=6:4);
$^1$H-NMR (CDCl$_3$): δ 0.88 (t, J=6.9 Hz, 3H), 0.91 (t, J=7.2 Hz, 3H), 1.20-2.40 (m, 44H), 3.53 (dd, J=10.2, 2.4 Hz, 1H), 3.93-4.15 (m, 4H), 4.37-4.45 (m, 2H), 4.47-4.54 (m, 2H), 5.35-5.50 (m, 3H), 5.52-5.65 (m, 1H), 7.10 (m, 1H), 7.33 (t, J=7.8 Hz, 1H), 7.54 (m, 1H), 7.61 (m, 1H);
MASS: (FAB, Pos.) 731 (M+H)$^+$

Example 4 (4)

2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 3-(tetradecyloxy)benzoate (Compound 4-4)

TLC: Rf 0.48 (hexane:ethyl acetate=6:4);
$^1$H-NMR (CDCl$_3$): δ 0.88 (t, J=6.9 Hz, 3H), 0.91 (t, J=7.5 Hz, 3H), 1.20-2.40 (m, 48H), 3.53 (dd, J=10.2, 2.4 Hz, 1H), 3.93-4.15 (m, 4H), 4.37-4.45 (m, 2H), 4.47-4.54 (m, 2H), 5.35-5.50 (m, 3H), 5.52-5.65 (m, 1H), 7.10 (m, 1H), 7.33 (t, J=7.8 Hz, 1H), 7.54 (m, 1H), 7.61 (m, 1H);
MASS: (FAB, Pos.) 759 (M+H)$^+$

Example 4 (5)

2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 3-(hexadecyloxy)benzoate (Compound 4-5)

TLC: Rf 0.49 (hexane:ethyl acetate=6:4);
$^1$H-NMR (CDCl$_3$): δ 0.88 (t, J=6.9 Hz, 3H), 0.91 (t, 3H), 1.18-2.40 (m, 52H), 3.52 (dd, J=10.2, 2.4 Hz, 1H), 3.93-4.15

(m, 4H), 4.37-4.45 (m, 2H), 4.47-4.54 (m, 2H), 5.33-5.50 (m, 3H), 5.52-5.65 (m, 1H), 7.10 (m, 1H), 7.32 (t, J=7.8 Hz, 1H), 7.54 (m, 1H), 7.60 (m, 1H);

MASS: (FAB, Pos.) 787 (M+H)$^+$

Example 4 (6)

2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 3-(octadecyloxy)benzoate (Compound 4-6)

TLC: Rf 0.52 (hexane:ethyl acetate=6:4);
$^1$H-NMR (CDCl$_3$): δ 0.88 (t, J=6.9 Hz, 3H), 0.91 (t, J=7.5 Hz, 3H), 1.18-2.40 (m, 56H), 3.52 (dd, J=10.2, 2.4 Hz, 1H), 3.93-4.16 (m, 4H), 4.37-4.45 (m, 2H), 4.47-4.54 (m, 2H), 5.30-5.50 (m, 3H), 5.52-5.63 (m, 1H), 7.09 (m, 1H), 7.32 (t, J=7.8 Hz, 1H), 7.53 (m, 1H), 7.60 (m, 1H);

MASS: (FAB, Pos.) 815 (M+H)$^+$

Example 4 (7)

2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 2-(pentadecyloxy)benzoate (Compound 4-7)

TLC: Rf 0.32 (hexane:ethyl acetate:methanol=7:2:1);
$^1$H-NMR (CDCl$_3$): δ 0.88 (t, =7.2 Hz, 3H), 0.91 (t, J=7.2 Hz, 3H), 1.20-2.40 (m, 50H), 3.52 (m, 1H), 3.90-4.15 (m, 4H), 4.39 (m, 2H), 4.48 (m, 2H), 5.52-5.65 (m, 4H), 6.90-7.00 (m, 2H), 7.44 (m, 1H), 7.77 (dd, J=8.1, 2.1 Hz, 1H);

MASS: (FAB, Pos.) 773 (M+H)$^+$

Example 4 (8)

2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 4-(decyloxy)benzoate (Compound 4-8)

TLC: Rf 0.47 (hexane:ethyl acetate=6:4);
$^1$H-NMR (CDCl$_3$): δ 0.88 (t, J=7.2 Hz, 3H), 0.91 (t, J=7.5 Hz, 3H), 1.18-2.40 (m, 40H), 3.52 (dd, J=9.9, 2.1 Hz, 1H), 3.93-4.16 (m, 4H), 4.36-4.43 (m, 2H), 4.44-4.53 (m, 2H), 5.33-5.65 (m, 4H), 6.89 (d, J=8.7 Hz, 2H), 7.97 (d, J=8.7 Hz, 2H);

MASS: (FAB, Pos.) 703 (M+1-1)$^+$

Example 4 (9)

2-{[(5Z)-7-{(1R,2R,3R,5R)-5-chloro-2-[(1E,4S)-4-(1-ethylcyclobutyl)-4-hydroxy-1-buten-1/1]-3-hydroxycyclopentyl}-5-heptenoyl]oxy}ethyl 4-(dodecyloxy)benzoate (Compound 4-9)

TLC: Rf 0.45 (hexane:ethyl acetate=6:4);
$^1$H-NMR (CDCl$_3$): δ 0.88 (t, J=6.9 Hz, 3H), 0.91 (t, J=7.5 Hz, 3H), 1.18-2.40 (m, 40H), 3.52 (dd, J=10.2, 2.7 Hz, 11.1), 3.94-4.16 (m, 4H), 4.36-4.44 (m, 2H), 4.44-4.52 (m, 2H), 5.35-5.65 (m, 4H), 6.89 (d, J=9.0 Hz, 2H), 7.96 (d, J=9.0 Hz, 2H);

MASS: (FAB, Pos.) 731 (M+H)$^+$

Example 4 (10)

2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 4-(tetradecyloxy)benzoate (Compound 4-10)

TLC: Rf 0.49 (hexane:ethyl acetate=6:4);
$^1$H-NMR (CDCl$_3$): δ 0.88 (t, J=6.9 Hz, 3H), 0.91 (t, J=7.2 Hz, 3H), 1.18-2.40 (m, 48H), 3.52 (dd, J=10.2, 2.4 Hz, 1H), 3.94-4.16 (m, 4H), 4.36-4.44 (m, 2H), 4.44-4.52 (m, 2H), 5.35-5.65 (m, 4H), 6.89 (d, J=9.0 Hz, 2H), 7.96 (d, J=9.0 Hz, 21-1);

MASS: (FAB, Pos.) 759 (M+H)$^+$

Example 4 (11)

2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 4-(pentadecyloxy)benzoate (Compound 4-11)

TLC: Rf 0.40 (hexane:ethyl acetate=0.6:4);
$^1$H-NMR (CDCl$_3$): δ 0.88 (t, J=6.6 Hz, 3H), 0.92 (t, J=7.5 Hz, 3H), 1.15-2.40 (m, 50H), 3.53 (d, 1H), 3.92-4.15 (m, 4H), 4.36-4.44 (m, 2H), 4.45-4.52 (m, 2H), 535-5.65 (m, 4H), 6.90 (d, J=9.0 Hz, 2H), 7.97 (d, J=9.0 Hz, 2H);

MASS: (FAB, Pos.) 773 (M+H)$^+$

Example 4 (12)

3-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}propyl 4-(pentadecyloxy)benzoate (Compound 4-12)

TLC: Rf 0.62 (hexane:ethyl acetate=6:4);
$^1$H-NMR(CDCl$_3$): δ 0.88 (t, J=6.9 Hz, 3H), 0.91 (t, J=7.2 Hz, 3H), 1.15-2.35 (m, 52H), 3.52 (dd, J=10.2, 2.4 Hz, 1H), 3.95-4.14 (m, 4H), 4.24 (t, J=6.3 Hz, 2H), 4.36 (t, J=6.3 Hz, 2H), 5.37-5.63 (m, 4H), 6.89 (d, J=8.7 Hz, 2H), 7.95 (d, J=8.7 Hz, 2H);

MASS: (FAB, Pos.) 787 (M+H)$^+$

Example 4 (13)

2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 4-(hexadecyloxy)benzoate (Compound 4-13)

TLC: Rf 0.61 (hexane:ethyl acetate=6:4);
$^1$H-NMR (CDCl$_3$): δ 0.88 (t, J=6.9 Hz, 3H), 0.91 (t, J=7.5 Hz, 3H), 1.15-2.40 (m, 52H), 3.53 (dd, 1H), 3.92-4.17 (m, 4H), 4.36-4.44 (m, 2H), 4.45-4.52 (m, 2H), 5.35-5.65 (m, 4H), 6.90 (d, J=8.4 Hz, 2H), 7.97 (d, J=8.4 Hz, 21-1);

MASS: (FAB, Pos.) 919 (M+Cs)$^+$

Example 4 (14)

2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 4-(octadecyloxy)benzoate (Compound 4-14)

TLC: Rf 0.60 (hexane:ethyl acetate=6:4);
$^1$H-NMR (CDCl$_3$): δ 0.88 (t, J=6.9 Hz, 3H), 0.91 (t, J=1.5 Hz, 3H), 1.15-2.40 (m, 56H), 3.52 (dd, J=10.5, 2.1 Hz, 1H), 3.94-4.16 (m, 4H), 4.36-4.43 (m, 2H), 4.44-4.51 (m, 2H), 5.34-5.65 (m, 4H), 6.89 (d, J=9.0 Hz, 2H), 7.96 (d, 21-1);
MASS: (FAB, Pos.) 947 (M+Cs)$^+$

Example 4 (15)

(2R)-1-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}-2-propyl 4-(tetradecyloxy)benzoate (Compound 4-15)

TLC: Rf 0.32 (hexane:ethyl acetate=85:15);
$^1$H-NMR (CDCl$_3$): δ 0.88 (t, J=6.6 Hz, 3H), 0.91 (t, J=7.2 Hz, 3H), 1.18-2.37 (m, 52H), 3.52 (m, 1H), 3.94-4.14 (m, 4H), 4.20-4.27 (m, 2H), 5.27-5.48 (m, 3H), 5.51-5.64 (m, 1H), 6.89 (d, J=19.0 Hz, 2H), 7.95 (d, J=9.0 Hz, 2H);
MASS: (FAB, Pos.) 905 (M+Cs)$^+$

Example 5

3-hexadecylbenzoic acid (Compound 5)

Meta-toluic acid (4.0 g) was dissolved in tetrahydrofuran (98 mL). Thereto, 2M lithium diisopropylamide (59 mL) was added at room temperature, followed by stirring for 1 hour. Thereto, 1-bromo pentadecane (9.4 mL) was added, followed by stirring at room temperature for 21 hours. The reaction solution was poured to 1N hydrochloric acid, followed by extraction with ethyl acetate. The organic layer was washed with aqueous saturated sodium chloride solution, dried with anhydrous sodium sulfate, and concentrated under reduced pressure. The obtained residue was purified by silica gel column chromatography (hexane:ethyl acetate=4:1) to obtain the title compound (3.7 g) having the following physical property values.
TLC: Rf 0.44 (hexane:ethyl acetate=2:1);
$^1$H-NMR (CDCl$_3$): δ 0.88 (t, 0.1-6.9 Hz, 3H), 1.19-1.32 (m, 27H), 1.61-1.66 (m, 2H), 2.66 (t, J=7.8 Hz, 2H), 7.34-7.43 (m, 2H), 7.90-7.92 (m, 2H)

Example 6

2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 3-hexadecylbenzoate (Compound 6)

By the same procedure as a series of reactions of Example 3→Example 4 using Compound 5 instead of Compound 2, and using 2-bromo-1-ethanol instead of 3-bromo-1-propanol, the title compound having the following physical property values was obtained.
TLC: Rf 0.63 (hexane:ethyl acetate=2:3);
$^1$H-NMR (CDCl$_3$): δ 0.86-0.94 (m, 614), 1.19-2.39 (m, 52H), 2.65 (t, J=7.5 Hz, 2H), 3.54-3.51 (m, 1H), 3.95-4.13 (m, 2H), 4.40-4.41 (m, 2H), 4.50-4.52 (m, 2H), 5.37-5.47 (m, 3H), 5.54-5.64 (m, 1H), 7.31-7.39 (m, 2H), 7.82-7.84 (n, 2H);
MASS: (FAB, Pos.) 771 (M+H)$^+$.

Example 6 (1)-6 (4)

By the same procedure as a series of reactions of Example 5→Example 6 using meta-toluic acid or a corresponding substituted benzoic acid, and using 2-bromo-1-ethanol or a corresponding alcohol, the following compound was obtained.

Example 6 (1)

3-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}propyl 3-hexadecylbenzoate (Compound 6-1)

TLC: Rf 0.61 (hexane:ethyl acetate=2:3);
$^1$H-NMR (CDCl$_3$): δ 0.88-0.94 (m, 6H), 1.19-2.35 (m, 54H), 2.64 (t, J=7.5 Hz, 2H), 3.51-3.54 (m, 1H), 3.96-4.13 (m, 2H), 4.24 (t, J=6.3 Hz, 2H), 4.39 (t, J=6.3 Hz, 2H), 5.37-5.63 (m, 4H), 7.30-7.38 (m, 2H), 7.83 (m, 2H);
MASS: (FAB, Pos.) 785 (M+H)$^+$

Example 6 (2)

4-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}butyl 3-hexadecylbenzoate (Compound 6-2)

TLC: Rf 0.65 (hexane:ethyl acetate=2:3);
$^1$H-NMR (CDCl$_1$): δ 0.85-0.94 (m, 6H), 1.19-2.35 (m, 56H), 2.65 (t, J=7.5 Hz, 2H), 3.52-3.55 (m, 1H), 3.97-4.16 (m, 4H), 4.34 (t, J=6.3 Hz, 2H), 5.37-5.64 (m, 4H), 7.30-7.38 (m, 2H), 7.82-7.84 (m, 2H);
MASS: (FAB, Pos.) 799 (M+H)$^+$

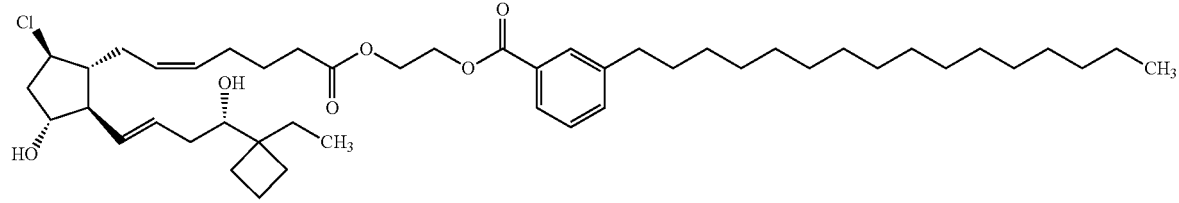 [SMILES: CCCCCCCCCCCCCCCCc1cccc(C(=O)OCCOC(=O)CCC/C=C\C[C@@H]2[C@@H](/C=C/C[C@H](O)C3(CC)CCC3)[C@H](O)C[C@H]2Cl)c1]

Example 6 (3)

2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 4-hexadecylbenzoate (Compound 6-3)

TLC: Rf 0.64 (hexane:ethyl acetate=2:3);
$^1$H-NMR (CDCl$_3$): δ 0.86-0.98 (m, 6H), 1.25-2.39 (m, 52H), 2.65 (t, J=7.8 Hz, 2H), 3.51-3.57 (m, 1H), 3.96-4.03

(m, 1H), 4.06-4.13 (m, 1H), 4.39-4.42 (m, 2H), 4.49-4.52 (m, 2H), 5.37-5.47 (m, 3H), 5.55-5.64 (m, 1H), 7.24 (d, J=8.4 Hz, 2H), 7.94 (d, J=8.4 Hz, 2H);

MASS: (FAB, Pos.) 771 (M+H)$^+$

Example 6 (4)

3-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}propyl 4-hexadecylbenzoate (Compound 6-4)

TLC: Rf 0.62 (hexane:ethyl acetate=2:3);
$^1$H-NMR (CDCl$_3$): δ 0.86-0.94 (m, 6H), 1.25-2.35 (m, 54H), 2.65 (t, J=7.5 Hz, 2H), 3.51-3.55 (m, 1H), 3.97-4.04 (m, 1H), 4.07-4.13 (m, 1H), 4.24 (t, 0.1-6.3 Hz, 2H), 4.39 (t, J=6.3 Hz, 2H), 5.38-5.48 (m, 3H), 5.55-5.65 (m, 1H), 7.23 (d, J=8.4 Hz, 2H), 7.93 (d, J=8.4 Hz, 2H);
MASS: (FAB, Pos.) 785 (M+H)$^+$

Example 7 methyl(4-pentadecylphenyl)carbamate (Compound 7)

To the solution of 4-pentadecanylaniline (3.4 g) in dichloromethane (60 mL), methyl chloroformate (1.1 mL) and the solution of potassium carbonate (7.8 g) in water (110 mL) were added at 0° C., followed by stirring at room temperature for 14 hours. The reaction solution was poured to water, followed by extraction with dichloroethane. The organic layer was washed sequentially with 2N hydrochloric acid, water and an aqueous saturated sodium chloride solution, and dried with anhydrous magnesium sulfate. The reaction solution was concentrated under reduced pressure to obtain the title compound (3.9 g) having the following physical property values.

TLC: Rf: 0.63 (hexane:ethyl acetate=4:1);
$^1$H-NMR (CDCl$_3$): δ 0.88 (t, J=6.9 Hz, 3H), 1.18-1.65 (m, 26H), 2.55 (m, 2H), 3.76 (s, 3H), 6.50 (br s, 1H), 7.10 (d, J=8.4 Hz, 2H), 7.22-7.28 (m, 2H).

Example 8

N-methyl-4-pentadecylaniline (Compound 8)

Compound 7 (3.9 g) was dissolved in tetrahydrofuran (55 mL). Lithium hydride aluminum (620 mg) was carefully added thereto and the reaction solution was refluexed with heating for 2 hours. After cooling the reaction solution to room temperature, 2N aqueous sodium hydroxide solution (3 mL) was added carefully, further tetrahydrofuran and anhydrous magnesium sulfate were added, followed by stirring for 1 hour. The reaction solution was filtered with Celite (brand name) and the filtrate was concentrated under reduced pressure. The obtained residue was purified by silica gel column chromatography (hexane:ethyl acetate=8:1) to obtain the title compound (3.4 g) having the following physical property values.

TLC Rf 0.54 (hexane:ethyl acetate=8:1);
$^1$H-NMR (CDCl$_3$): δ 0.88 (t, J=6.9 Hz, 3H), 1.15-1.40 (m, 24H), 1.46-1.65 (m, 2H), 2.49 (m, 2H), 2.82 (s, 3H), 3.56 (m, 1H), 6.55 (d, J=8.4 Hz, 2H), 6.99 (d, J=8.4 Hz, 2H).

Example 9

2-bromo-N-methyl-N-(4-pentadecylphenyl)acetamide (Compound 9)

Compound 8 (1.5 g) was dissolved in dichloromethane (10 mL). Potassium carbonate (980 mg) and the solution of bromoacetyl chloride (890 mg) in dichloromethane (5 mL) was added thereto at 0° C., followed by stirring for 1.5 hours. The reaction solution cooled with ice was poured into 1N hydrochloric acid, followed by extraction with dichloromethane. The organic layer was washed with an aqueous saturated sodium chloride solution, dried with anhydrous magnesium sulfate and concentrated under reduced pressure. The obtained residue was purified by silica gel column chromatography (hexane:ethyl acetate=4:1) to obtain the title compound (1.7 g) having the following physical property values.

TLC: Rf 0.36 (hexane:ethyl acetate=4:1);
$^1$H-NMR (CDCl$_3$): δ 0.88 (t, J=7.2 Hz, 3H), 1.20-1.42 (m, 24H), 1.62 (m, 2H), 2.63 (m, 2H), 3.28 (s, 3H), 3.67 (s, 21.1), 7.05-7.26 (m, 4H).

Example 10

2-[methyl(4-pentadecylphenyl)amino]-2-oxoethyl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate (Compound 10)

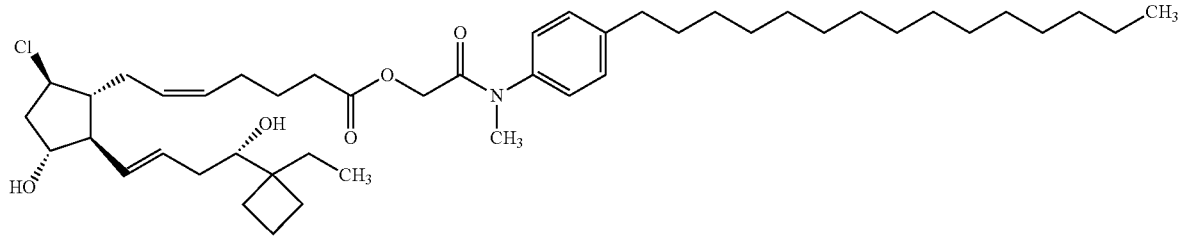 [SMILES: CCCCCCCCCCCCCCCc1ccc(N(C)C(=O)COC(=O)CCC/C=C\C[C@@H]2[C@@H](/C=C/C[C@H](O)C3(CC)CCC3)[C@H](O)C[C@H]2Cl)cc1]

By the same procedure as Example 4 using Compound 9 instead of Compound 3, the title compound having the following physical property value was obtained.

TLC: Rf 0.48 (hexane:ethyl acetate=1:1);
$^1$H-NMR (CDCl$_3$): δ0.88 (t, J=7.2 Hz, 3H), 0.92 (t, J=7.2 Hz, 3H), 1.15-1.52 (m, 26H), 1.52-2.46 (m, 24H), 2.64 (m, 2H), 3.25 (s, 3H), 3.53 (d, J=9.6 Hz, 1H), 3.98-4.16 (m, 2H), 4.38 (s, 2H), 5.32-5.50 (m, 3H), 5.51-5.67 (m, 1H), 7.14 (d, J=8.4 Hz, 2H), 7.22 (d, J=8.4 Hz, 2H);

MS (FAB, Pos.): 756 (M+H)$^+$.

Example 11

(10-bromodecyl)benzene (Compound 11)

In diethylether (200 mL), 10-phenyl-1-decanol (10 g) was dissolved, phosphorus tribromide (4.0 mL) was carefully added thereto, at 0° C., followed by stirring at room temperature for 6 hours. Water was added carefully to the reaction solution, followed by extraction with tert-buthylmethylether. The organic layer was washed with water, dried with anhydrous sodium sulfate and concentrated under reduced pressure. The obtained residue was purified by silica gel column chromatography (hexane:ethyl acetate=9:1) to obtain the title compound (7.0 g) having the following physical property values.

TLC: Rf 0.73 (hexane:ethyl acetate=5:1);

$^1$H-NMR (CDCl$_3$): δ 1.15-1.50 (m, 12H), 1.61 (m, 2H), 1.85 (m, 2H), 2.59 (m, 2H), 3.40 (t, J=6.9 Hz, 2H), 7.10-7.20 (m, 3H), 7.22-7.30 (m, 2H).

Example 12 triphenyl(10-phenyldecyl)phosphonium bromide (Compound 12)

Compound 11 (7.0 g) was dissolved in toluene (80 mL) and triphenylphosphine (6.8 g) was added thereto, followed by stirring at 100° C. for 12 hours. Triphenylphosphine (1.3 g) was further added, followed by stirring at 100° C. for 24 hours. After cooling the reaction solution to room temperature, the resulting precipitate was washed with toluene three times and the residue was dried under reduced pressure to obtain the title compound (7.2 g) having the following physical property values.

$^1$H-NMR (CDCl$_3$): δ 1.10-1.35 (m, 10H), 1.46-1.80 (m, 6H), 2.57 (m, 2H), 3.74-3.90 (m, 2H), 7.10-7.30 (m, 5H), 7.60-7.90 (m, 15H)

Example 13 benzyl(5-hydroxypentyl)methylcarbamate (Compound 13)

N-methyl-5-amino alcohol (5.6 g) was dissolved in 2N aqueous sodium hydroxide (25 mL) and benzyl chloroformate (8.8 mL) and 2N aqueous sodium hydroxide (31 mL) were added by portions at 0° C., followed by stirring at the same temperature for 1.5 hours. Concentrated hydrochloric acid was added to the reaction solution to adjust pH to about 4.0, followed by extraction with ethyl acetate. The organic layer was dried with anhydrous magnesium sulfate and concentrated under reduced pressure. The obtained residue was purified by silica gel column chromatography (hexane:ethyl acetate=1:1→1:2) to obtain the title compound (7.0 g) having the following physical property values.

TLC: Rf 0.49 (hexane:ethyl acetate=1:2);

$^1$H-NMR (CDCl$_3$): δ 1.10-1.68 (m, 7H), 2.91 (s, 3H), 3.28 (m, 2H), 3.60 (m, 2H), 5.11 (s, 2H), 7.22-7.38 (m, 5H).

Example 14 benzyl methyl(5-oxopentyl)carbamate (Compound 14)

Compound 13 (1.7 g) was dissolved in dichloromethane (21 mL), and triethylamine (4.8 mL) and dimethylsulfoxide (9.6 mL) was added thereto. Pyridine-sulfurtrioxide complex (2.8 g) was further added at 0° C. followed by stirring for 1.5 hours. Tert-butylmethyleter (60 mL) was added to the reaction solution and the solution was poured into water. The organic layer was washed sequentially with 1N hydrochloric acid, water and an aqueous saturated sodium chloride solution. The solution was dried with anhydrous sodium sulfate and concentrated under reduced pressure to have the title compound (1.7 g) having the following physical property values.

TLC: Rf 0.53 (hexane:ethyl acetate=1:1).

Example 15 benzyl methyl(15-phenylpentadec-5-en-1-yl)carbamate (Compound 15)

Compound 12 (6.5 g) was dissolved in tetrahydrofuran (18 mL). Potassium-tert-butoxide (1.2 g) was added thereto at 0° C., followed by stirring at room temperature for 30 minutes. After cooling the reaction solution to 0° C., the solution of Compound 14 (1.7 g) in tetrahydrofran (3 mL) was added drop wise thereto, followed by the stirring at the same temperature for 2 hours. To the reaction solution, tert-butylmethylether (40 mL) and water (30 mL) were added. The organic layer was washed with water and an aqueous saturated sodium chloride solution, dried with anhydrous magnesium sulfate and concentrated under reduced pressure. The obtained residue was purified by silica gel column chromatography (hexane:ethylacetate=1:1→1:2) to obtain the title compound (2.7 g) having the following physical property values.

TLC: Rf 0.45 (hexane:ethyl acetate=8:1);

$^1$H-NMR(CDCl$_3$): δ 1.20-1.40 (m, 14H), 1.42-1.65 (m, 4H), 1.85-2.10 (m, 4H), 2.59 (m, 2H), 2.90 (s, 3H), 3.20-3.34 (m, 2H), 5.11 (s, 2H), 5.22-5.42 (m, 2H), 7.10-7.40 (m, 10H).

Example 16

N-methyl-15-phenylpentadecane-1-amine (Compound 16)

Compound 15 (2.6 g) was dissolved in ethanol (20 mL) and 5% palladium carbon (260 mg) was added thereto, followed by stirring at room temperature for 3.5 hours under hydrogen atmosphere. The reaction solution was replaced with argon atmosphere, filtered with Celite (brand name) and concentrated under reduced pressure to obtain the title compound (1.2 g) having the following physical property values.

TLC: Rf 0.53 (n-butanol:acetic acid:water=4:2:1);

$^1$H-NMR (CDCl$_3$): δ 1.15-1.75 (m, 26H), 2.42 (s, 3H), 2.50-2.63 (m, 4H), 7.12-7.30 (m, 5H).

Example 17

2-[methyl(15-phenylpentadecyl)amino]-2-oxoethyl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate (Compound 17)

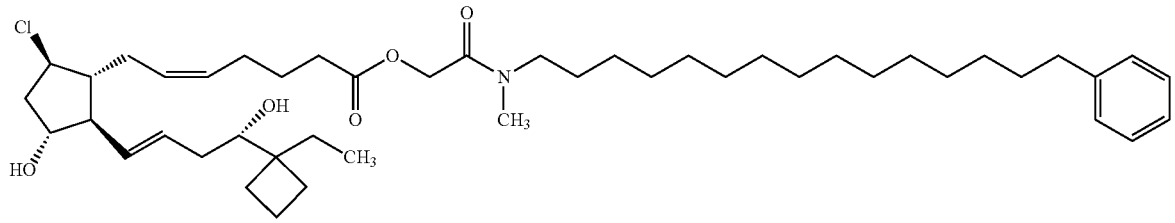 [SMILES: CCC1([C@@H](O)C/C=C/[C@@H]2[C@@H](C/C=C\CCCC(=O)OCC(=O)N(C)CCCCCCCCCCCCCCCc3ccccc3)[C@H](Cl)C[C@H]2O)CCC1]

By the same procedure as a series of reactions of Example 9→Example 10 using Compound 16 instead of Compound 8, the title compound having the following physical property value was obtained.

TLC: Rf 0.64 (hexane:ethyl acetate=1:2);
$^1$H-NMR (CDCl$_3$): δ 0.92 (t, J=7.5 Hz, 3H), 1.15-2.50 (m, 50H), 2.60 (m, 214), 2.92 and 2.93 (each s, 3H), 3.17 (m, 1H), 3.34 (m, 1H), 3.52 (d, 3=9.6 Hz, 1H), 3.98-4.15 (m, 2H), 4.69 and 4.72 (each s, 2H), 5.33-5.50 (m, 3H), 5.50-5.68 (m, 1H), 7.10-7.20 (m, 3H), 7.20-7.30 (m, 21-1);
MASS: (FAB, Pos.) 756 (M+H)$^+$.

Example 17 (1)-17 (6)

By the same procedure as Example 17 using a corresponding amine instead of Compound 16, the following compounds are obtained.

Example 17 (1)

2-[methyl(tetradecyl)amino]-2-oxoethyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate (Compound 17-1)

TLC: Rf 0.41 (hexane:ethyl acetate=2:3);
$^1$H-NMR (CDCl$_3$): δ 0.88 (t, J=6.9 Hz, 3H), 0.92 (t, J=7.5 Hz, 3H), 1.15-2.52 (m, 48H), 2.92 and 2.93 (each s, 3H), 3.17 (m, 1H), 3.34 (m, 1H), 3.52 (m, 1H), 3.98-4.14 (m, 2H), 4.70 (m, 2H), 5.34-5.52 (m, 3H), 5.58 (m, 1H);
MASS: (FAB, Pos.) 666 (M+H)$^+$.

Example 17 (2)

2-[hexadecyl(methyl)amino]-2-oxoethyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate (Compound 17-2)

TLC: Rf 0.40 (hexane:ethyl acetate=2:3);
$^1$H-NMR (CDCl$_3$): δ0.88 (t, J=6.9 Hz, 3H), 0.92 (t, J=7.5 Hz, 3H), 1.15-2.52 (m, 52H), 2.92 and 2.93 (each s, 3H), 3.17 (m, 1H), 3.34 (m, 1H), 3.52 (m, 1H), 3.98-4.14 (m, 2H), 4.70 (m, 2H), 5.34-5.52 (m, 3H), 5.53-5.66 (m, 1H);
MASS: (FAB, Pos.) 694 (M+H)$^+$.

Example 17 (3)

2-[methyl(octadecyl)amino]-2-oxoethyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate (Compound 17-3)

TLC: Rf 0.47 (hexane:ethyl acetate=1:1);
$^1$H-NMR (CDCl$_3$): δ0.88 (t, J=6.9 Hz, 3H), 0.92 (t, J=7.2 Hz, 3H), 1.12-1.34 (m, 32H), 1.35-1.90 (m, 7H), 1.90-2.38 (m, 14H), 2.41-2.58 (m, 3H), 2.92 and 2.94 (each s, 3H), 3.17 (m, 1H), 3.34 (m, 1H), 3.53 (d, J=9.9 Hz, 1H), 3.95-4.15 (m, 2H), 4.67 and 4.72 (each s, 2H), 5.35-5.51 (m, 3H), 5.52-5.66 (m, 1H);
MASS: (FAB, Pos.) 722 (M+H)$^+$.

Example 17 (4)

2-[icosyl(methyl)amino]-2-oxoethyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate (Compound 17-4)

TLC: Rf 0.36 (hexane:ethyl acetate=1:1);
$^1$H-NMR (CDCl$_3$): δ0.88 (t, J=6.9 Hz, 3H), 0.92 (t, J=7.2 Hz, 3H), 1.12-2.58 (m, 60H), 2.92 and 2.94 (each s, 3H), 3.17 (m, 1H), 3.34 (m, 1H), 3.53 (d, J=9.9 Hz, 1H), 3.95-4.15 (m, 2H), 4.67 and 4.72 (each s, 2H), 5.35-5.51 (m, 3H), 5.52-5.66 (m, 1H);
MASS: (FAB, Pos.) 750 (M+H)$^+$.

Example 17 (5)

2-[ethyl(octadecyl)amino]-2-oxoethyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate (Compound 17-5)

TLC: Rf 0.33 (hexane:ethyl acetate 6:4);
$^1$H-NMR (CDCl$_3$): δ0.88 (t, J=7.2 Hz, 3H), 0.92 (t, J=7.5 Hz, 3H), 1.12 (t, J=6.9 Hz, 3H), 1.17-2.50 (m, 56H), 3.08-3.42 (m, 4H), 3.53 (m, 1H), 3.98-4.14 (m, 2H), 4.69 and 4.71 (each s, 2H), 5.35-5.51 (m, 3H), 5.52-5.66 (m, 1H);
MASS: (FAB, Pos.) 736 (M+H)$^+$.

Example 17 (6)

2-[octadecyl(phenyl)amino]-2-oxoethyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate (Compound 17-6)

TLC: Rf 0.43 (hexane:ethyl acetate=3:2);
$^1$H-NMR (CDCl$_3$): δ0.88 (t, J=6.9 Hz, 3H), 0.92 (t, J=7.5 Hz, 3H), 1.12-2.45 (m, 56H), 3.52 (d, J=9.9 Hz, 1H), 3.66 (m, 2H), 3.96-4.15 (m, 2H), 4.31 (s, 2H), 5.34-5.49 (m, 3H), 5.52-5.65 (m, 1H), 7.18-7.27 (m, 2H), 7.33-7.48 (m, 3H);
MASS: (FAB, Pos.) 784 (M+H)$^+$.

Example 18

1-bromooctadec-2-in (Compound 18)

Thereto, 2-octadecyn-1-ol (510 mg) was dissolved in dichloromethane (20 mL) and carbontetrabromide (960 mg) and triphenylphosphine (660 mg) were added at 0° C., followed by stirring at room temperature for 2 hours. The reaction solution was concentrated under reduced pressure and the obtained residue was purified by silica gel column chromatography (hexane:ethyl acetate-99:1→95:5) to obtain the title compound (630 mg) having the following physical property values.
TLC: Rf 0.76 (hexane:ethyl acetate=95:5);
$^1$H-NMR (CDCl$_3$): δ0.88 (t, J=6.9 Hz, 3H), 1.20-1.60 (m, 26H), 2.23 (m, 2H), 3.93 (t, J—2.4 Hz, 2H),

Example 19

2-octadecyn-1-yl(5Z)-7-{(1R,2R,3R,5R)-5-chloro-2-[(1E,4S)-4-(1-ethylcyclobutyl), 4-hydroxy-1-buten-1-yl]-3-hydroxycyclopentyl}-5-heptenoate (Compound 19)

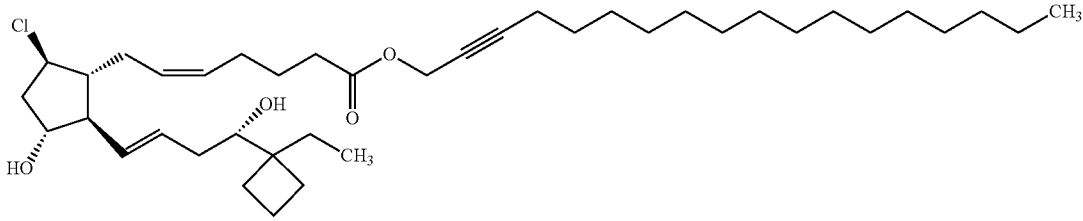 [SMILES: CCCCCCCCCCCCCCCC#CCOC(=O)CCC/C=C\C[C@@H]1[C@@H](/C=C/C[C@H](O)C2(CC)CCC2)[C@H](O)C[C@H]1Cl]

By the same procedure as Example 4 using Compound 18 instead of Compound 3, the title compound having the following physical property value was obtained.
TLC: Rf 0.57 (hexane:ethyl acetate=6:4);
$^1$H-NMR (CDCl$_3$): δ0.88 (t, J=6.9 Hz, 3H), 0.92 (t, J=7.5 Hz, 3H), 1.15-2.40 (m, 52H), 3.53 (dd, J=10.5, 2.4 Hz, 1H), 3.95-4.16 (m, 2H), 4.66 (t, J=2.1 Hz, 2H), 5.35-5.66 (m, 4H);
MASS: (FAB, Pos.) 647 (M+H)$^+$.

Example 19 (1)-19 (8)

By the same procedure as a series of reactions of Example 18→Example 19 using a corresponding alcohol instead of 2-octadecyn-1-ol, the following compounds are obtained.

Example 19 (1)

2-pentadecyn-1-yl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate (Compound 19-1)

TLC: Rf 0.53 (hexane:ethyl acetate=6:4);
$^1$H-NMR (CDCl$_3$): δ0.88 (t, J=6.9 Hz, 3H), 0.92 (t, J=7.5 Hz, 3H), 1.18-2.40 (m, 46H), 3.53 (dd, J=10.5, 2.4 Hz, 1H), 3.95-4.16 (m, 2H), 4.66 (t, J=2.1 Hz, 2H), 5.35-5.66 (m, 4H);
MASS: (FAB, Pos.) 605 (M+H)$^+$.

Example 19 (2)

2-heptadecyn-1-yl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate (Compound 19-2)

TLC: Rf 0.55 (hexane:ethyl acetate=6:4);
$^1$H-NMR (CDCl$_3$): δ0.88 (t, J=6.9 Hz, 3H), 0.92 (t, J=7.2 Hz, 3H), 1.15-2.40 (m, 50H), 3.53 (dd, J=10.2, 2.1 Hz, 1H), 4.00 (m, 1H), 4.10 (q, 1H), 4.66 (t, J=2.1 Hz, 2H), 5.35-5.65 (m, 4H);
MASS: (FAB, Pos.) 633 (M+H)$^+$.

Example 19 (3)

2-nonadecyn-1-yl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate (Compound 19-3)

TLC: Rf 0.57 (hexane:ethyl acetate=6:4);
$^1$H-NMR (CDCl$_3$): δ0.88 (t, J=6.9 Hz, 3H), 0.92 (t, J=7.2 Hz, 3H), 1.20-2.40 (m, 54H), 3.54 (dd, J=10.2, 2.4 Hz, 1H), 4.00 (m, 1H), 4.10 (q, J=6.9 Hz, 1H), 4.67 (t, J=2.1 Hz, 2H), 5.35-5.65 (m, 4H);
MASS: (FAB, Pos.) 661 (M+H)$^+$.

Example 19 (4)

2-henicosyn-1-yl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate (Compound 19-4)

TLC: Rf 0.30 (hexane:ethyl acetate=7:3);
$^1$H-NMR (CDCl$_3$): δ0.88 (t, J=7.2 Hz, 3H), 0.92 (t, J=7.5 Hz, 3H), 1.15-2.35 (m, 56H), 2.35 (t, J=7.5 Hz, 2H), 3.53 (dd, J=9.9, 2.1 Hz, 1H), 4.00 (m, 1H), 4.10 (m, 1H), 4.66 (t, J=2.1 Hz, 2H), 5.35-5.65 (m, 4H);
MASS: (FAB, Pos.) 821 (M+Cs)$^+$.

Example 19 (5)

(2E)-2-hexadecen-1-yl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate (Compound 19-5)

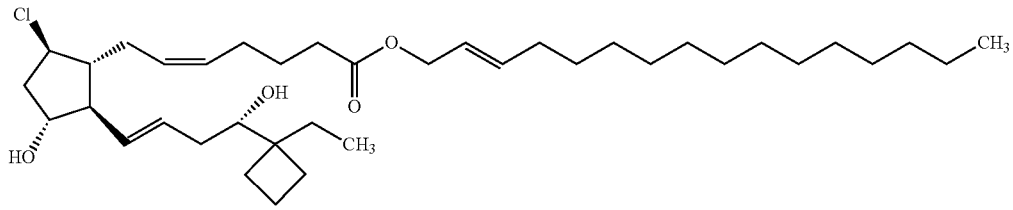 [SMILES: CCCCCCCCCCCCC/C=C/COC(=O)CCC/C=C\C[C@@H]1[C@@H](/C=C/C[C@H](O)C2(CC)CCC2)[C@H](O)C[C@H]1Cl]

TLC: Rf 0.50 (hexane:ethyl acetate=6:4);
$^1$H-NMR (CDCl$_3$): δ0.88 (t, J=6.6 Hz, 3H), 0.92 (t, J=7.2 Hz, 3H), 1.17-2.40 (m, 48H), 3.53 (dd, J=9.9, 2.1 Hz, 1H), 3.95-4.16 (m, 2H), 4.50 (d, J=6.3 Hz, 2H), 5.36-5.82 (m, 6H);
MASS: (FAB, Pos.) 621 (M+H)$^+$.

Example 19 (6)

(2E)-2-octadecen-1-yl(5Z)-7{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate (Compound 19-6)

TLC: Rf 0.45 (hexane:ethyl acetate=2:1);
$^1$H-NMR (CDCl$_3$): δ0.88 (t, J=7.2 Hz, 3H), 0.92 (t, J=7.5 Hz, 3H), 1.10-2.37 (m, 52H), 3.53 (d, J=10.2 Hz, 1H), 3.94-4.16 (m, 2H), 4.50 (dd, 0.9 Hz, 2H), 5.34-5.66 (m, 5H), 5.68-5.82 (m, 1H);
MASS: (FAB, Pos.) 649 (M+H)$^+$.

Example 19 (7)

(2E)-2-icosen-1-yl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate (Compound 19-7)

TLC: Rf 0.52 (hexane:ethyl acetate=6:4);
$^1$H-NMR (CDCl$_3$): δ0.88 (t, J=7.2 Hz, 3H), 0.92 (t, J=7.5 Hz, 3H), 1.15-2.40 (m, 56H), 3.53 (dd, J=9.6, 1.8 Hz, 1H), 3.95-4.16 (m, 2H), 4.50 (dd, J=6.6, 0.9 Hz, 2H), 5.34-5.83 (m, 6H);
MASS: (FAB, Pos.) 677 (M+H)$^+$.

Example 19 (8)

(2Z)-2-octadecen-1-yl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate (Compound 19-8)

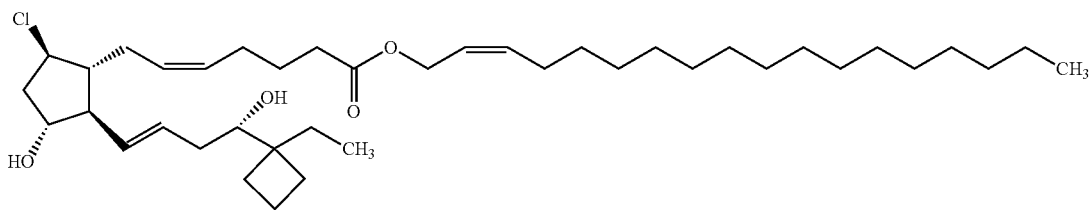 [SMILES: CCCCCCCCCCCCCCC/C=C\COC(=O)CCC/C=C\C[C@@H]1[C@@H](/C=C/C[C@H](O)C2(CC)CCC2)[C@H](O)C[C@H]1Cl]

TLC: Rf 0.56 (hexane:ethyl acetate=6:4);
$^1$H-NMR (CDCl$_3$): δ0.88 (t, J=7.2 Hz, 3H), 0.92 (t, J=7.5 Hz, 3H), 1.10-2.48 (m, 52H), 3.53 (m, 1H), 3.94-4.17 (m, 2H), 4.61 (d, J=6.6 Hz, 2H), 5.34-5.70 (m, 6H);
MASS: (FAB, Pos.) 649 (M+H)$^+$.

Example 20 (1)-20 (2)

By the same procedure as Example 4 using a corresponding compound instead of Compound 3, the following compound was obtained.

Example 20 (1)

undecyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate (Compound 20-1)

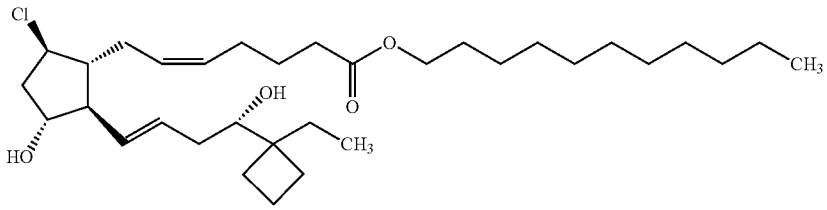 [SMILES: CCCCCCCCCCCOC(=O)CCC/C=C\C[C@@H]1[C@@H](/C=C/C[C@H](O)C2(CC)CCC2)[C@H](O)C[C@H]1Cl]

TLC: Rf 0.48 (hexane:ethyl acetate=1:1);
$^1$H-NMR (CDCl$_3$): δ0.88 (t, J=6.6 Hz, 3H), 0.92 (t, J=7.5 Hz, 3H), 1.20-2.20 (m, 42H), 3.54 (m, 1H), 3.96-4.17 (m, 4H), 5.36-5.72 (m, 4H);
MASS: (FAB, Pos.) 553 (M+H)$^+$.

Example 20 (2)

octadecyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate (Compound 20-2)

TLC: Rf 0.70 (hexane:ethyl acetate:acetic acid=30:60:1);
$^1$H-NMR (CDCl$_3$): δ0.88 (t, J=7.2 Hz, 3H), 0.92 (t, J=7.5 Hz, 3H), 1.05-2.45 (m, 56H), 3.53 (d, J=9.6 Hz, 1H), 4.05 (t, J=6.9 Hz, 2H), 3.95-4.16 (m, 2H), 5.34-5.65 (m, 4H);
MASS: (FAB, Pos.) 651 (M+H)$^+$.

Example 21

1-(2-(pentadecyloxy)phenyl)ethanone (Compound 21)

In acetonitrile (50 mL), 2-hydroxyacetophenone (3.9 g) and 1-bromopentadecane (8.4 g) were dissolved. Potassium carbonate (7.9 g) was added thereto and refluxed with heating for 48 hours. After cooling the reaction solution, it was diluted with ethylacetate and filtered with Celite (brand name). The filtrate was concentrated under reduced pressure and the obtained residue was purified by silica gel column chromatography (hexane:ethyl acetate=100:0→90:10). To the obtained solid, methanol was added, filtrated and dried under reduced pressure to obtain the title compound (8.1 g) having the following physical property values.
TLC: Rf 0.53 (hexane:ethyl acetate=9:1).

Example 22

2-bromo-1-(2-(pentadecyloxy)phenyl)ethanone (Compound 22)

The compound (600 mg) prepared in Example 21 was dissolved in toluene (4.0 mL), and bromine (280 mg) and acetic acid (2.0 mL) was added thereto, followed by stirring at room temperature for 2 hours. The reaction solution was diluted with ethyl acetate, washed sequentially with an aqueous saturated sodium bicarbonate solution, water and an aqueous saturated sodium chloride solution. The solution was dried with anhydrous magnesium sulfate and concentrated under reduced pressure to obtain the title compound (850 mg) having the following physical property values. The obtained compound was used in the next process without purifying.
TLC: Rf 0.53 (hexane:ethyl acetate=9:1).

Example 23

2-oxo-2-[2-(pentadecyloxy)phenyl]ethyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate (Compound 23)

By the same procedure as Example 4 using Compound 22 instead of Compound 3, the title compound having the following physical property values was obtained.
TLC: Rf 0.39 (hexane:ethyl acetate=6:4);
$^1$H-NMR (CDCl$_3$): δ0.80-0.95 (m, 6H), 1.15-2.43 (m, 47H), 2.51 (t, J=7.5 Hz, 2H), 3.45-3.60 (m, 1H), 3.95-4.20 (m, 5H), 5.27 (s, 2H), 5.35-5.70 (m, 4H), 6.97 (d, J=8.4 Hz, 1H), 7.03 (t, J=7.8 Hz, 1H), 7.50 (dt, J=1.8, 8.4 Hz, 1H), 7.93 (dd, J=1.8, 7.8 Hz, 1H);
MASS: (FAB, Pos.) 743 (M+H)$^+$.

Reference Example 1

N-(2-chloroethyl)-N-methyl-octadecyl ammonium chloride

Thionyl chloride (0.45 mL) was dissolved in 1,2-dichloroethane (3.0 mL). The solution of N-(2-hydroxyethyl)-N-methyl-octadecylamine (1.0 g) in 1,2-dichloroethane (7.0 mL) was added thereto at 0° C., followed by stirring at 50° C. for 30 minutes. The reaction solution was concentrated under reduced pressure and azeotrope was carried out with toluene twice to obtain the title compound (1.2 g) having the following physical property values.
TLC: Rf 0.53 (hexane:ethyl acetate=1:1);
$^1$H-NMR (CDCl$_3$): δ0.88 (t, J=7.2 Hz, 3H), 1.20-1.42 (m, 30H), 1.70-1.95 (m, 2H), 2.85 and 2.84 (each s, 3H), 2.91-3.19 (m, 2H), 3.28 (m, 1H), 3.45 (m, 1H), 4.05 (m, 2H).

Reference Example 2

2-[methyl(octadecyl)amino]ethyl(5Z)-7-{(1R,2R,3R,5R)-5-chloro-2-[(1E,4S)-4-(1-ethylcyclobutyl)-4-hydroxy-1-buten-1-yl]-3-hydroxypentyl}-5-heptenoate By the same process as Example 4 using the compound (560 mg) prepared in Reference Example 1 instead of Compound 3, the title compound (460 mg) having the following physical property values was obtained.
TLC: Rf 0.31 (hexane:ethyl acetate:methanol=1:1:0.05);

¹H-NMR (CDCl₃): δ0.88 (t, J=7.2 Hz, 3H), 0.92 (t, J=7.5 Hz, 3H), 1.18-2.42 (m, 61H), 2.61 (t, J=5.7 Hz, 2H), 3.53 (dd, J=9.9, 2.4 Hz, 1H), 3.96-4.20 (m, 4H), 5.35-5.66 (m, 4H).

Reference Example 3

N-(2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl)-N,N-di methyl-octadecyl ammonium bromide To the compound (350 mg) prepared in Reference Example 2, a solution of 2.6 M methyl bromide in tert-butylmethyleter (3.3 mL) was added at room temperature, followed by stirring at room temperature for 16 hours. After concentration of the reaction solution under reduced pressure, the obtained residue was washed with a solution (hexane:cyclohexane=3:1) (3.0 mL) by decantation five times and further washed with a solution (hexane:tert-butylmethyleter=5:1) (3.0 mL) by decantation five times. The obtained residue was dried under reduced pressure to obtain the title compound (280 mg) having the following physical property values.
TLC: Rf 0.46 (dichloromethane:methanol:acetic acid=5:1:0.1);
¹H-NMR (CDCl₃): δ0.88 (t, J=6.9 Hz, 3H), 0.91 (t, J=7.5 Hz, 3H), 1.20-2.44 (m, 55H), 3.34 (br s, 1H), 3.44 (s, 6H), 3.49-3.60 (m, 3H), 3.98-4.17 (m, 4H), 4.57 (m, 2H), 5.35-5.65 (m, 4H);
MASS: (FAB, Pos.) 722 (M+H)⁺, Reference Example 4

2-oxooctadecyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate By the same process as Example 4 using 1-bromooctadecane-2-one instead of Compound 3, the title compound having the following physical property values was obtained.
TLC: Rf 0.46 (hexane:ethyl acetate=6:4);
¹H-NMR (CDCl₃): δ0.88 (t, J=7.2 Hz, 3H), 0.92 (t, J=7.2 Hz, 3H), 1.16-2.48 (m, 54H), 3.53 (m, 1H), 3.95-4.15 (m, 2H), 4.65 (s, 2H), 5.35-5.65 (m, 4H);
MASS: (FAB, Pos.) 665 (M+H)⁺.

Reference Example 5

2-(dioctadecylamino)-2-oxoethyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate By the same process as Example 4 using 2-chloro-N,N-dioctadecylacetamide instead of Compound 3, the title compound having the following physical property values was obtained.
TLC: Rf 0.42 (hexane:ethyl acetate=3:2);
¹H NMR(CDCl₃): δ0.88 (t, J=7.2 Hz, 6H), 0.92 (t, J=7.5 Hz, 3H), 1.11-2.39 (m, 86H), 2.46 (t, J=7.3 Hz, 2H), 3.13 (dd, J=8.1, 7.4 Hz, 2H), 3.22-3.34 (m, 2H), 3.53 (d, 0.2 Hz, 1H), 3.97-4.17 (m, 2H), 4.69 (s, 2H), 5.34-5.52 (m, 3H), 5.51-5.69 (m, 1H);
MASS: (FAB, Pos.) 960 (M+H)⁺.

Reference Example 6

2-[docosyl(methyl)amino]-2-oxoethyl(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate By the same process as Example 17 using a corresponding amine instead of Compound 16, the title compound having the following physical property values was obtained.

TLC: Rf 0.36 (hexane:ethyl acetate=1:1);
¹H-NMR (CDCl₃): δ0.88 (t, J=6.9 Hz, 3H), 0.92 (t, J=7.2 Hz, 3H), 1.12-2.58 (m, 64H), 2.92 and 2.94 (each s, 3H), 3.17 (m, 1H), 3.34 (m, 1H), 3.53 (d, 1H), 3.95-4.15 (m, 2H), 4.67 and 4.72 (each s, 2H), 5.34-5.67 (m, 4H);
MASS: (FAB, Pos.) 778 (M+H)⁺.

Formulation Example (1) Effect of Additives on Particle Forming

Formulation Example 1-3

<Preparation Method>
To distilled water, Compound 4-11 dissolved in ethanol was added slowly, 5% glucose solution and 5% glucose solution containing 0.05% Tween 80 with stirring. The suspension was prepared so that the final concentration calculated in Compound A becomes 1.6 mg/mL. The particle concentration in the obtained suspension was 4.01 mM. The quantity of each component is as follows,

TABLE 1

| | Formulation Example 1 Weighed Value (mg) | Formulation Example 2 Weighed Value (mg) | Formulation Example 3 Weighed Value (mg) |
|---|---|---|---|
| Compound 4-11 | 6.2 | 6.2 | 6.2 |
| Ethanol | 0.1 mL | 0.1 mL | 0.1 mL |
| Distilled Water | 1.9 mL | | |
| 5% glucose solution | | 1.9 mL | |
| 5% glucose solution containing 0.05% Tween80 | | | 1.9 mL |

<Measuring Method of Particle Diameter>
The suspension was stored at 5° C. At 30 minutes and 24 hours after preparation, the particle diameter was measured with a laser diffraction grain size distribution measuring apparatus (SALD-2100: manufactured by Shimadzu Corp.) by dispersing suspension in distilled water.
Particle forming of Formulation Example 1 to 3 was evaluated by mean particle diameter (Dv: volume mean diameter) and particle distribution (PDT: indicator of the width of particle distribution. The smaller is the number and the smaller is the variation of particle distribution. PDI=Dv/Dn (number mean particle diameter)),
<Result>
The following describes mean particle diameter (Dv) and particle distribution (PDI) of Formulation Examples 1 to 3.

TABLE 2

| 30 min. after preparation | Dv (μm) | PDI |
|---|---|---|
| Formulation Example 1 | 1.588 | 2.6 |
| Formulation Example 2 | 1.688 | 2.8 |
| Formulation Example 3 | 1.458 | 2.5 |

TABLE 3

| 24 hours after preparation | Dv (μm) | PDI |
|---|---|---|
| Formulation Example 1 | 1.252 | 2.1 |
| Formulation Example 2 | 1.329 | 2.2 |
| Formulation Example 3 | 1.278 | 2.2 |

In any of Formulation Example 1 to 3, an increase of particle diameter with time was not observed and the particle was uniform and stable. Therefore, regardless of the existence of surfactants or additives, it was confirmed that the compound of the present invention forms very stable particle.

In the following evaluation, for the purpose of preventing particle adhesion to a preparation container, evaluations were performed with formulations using 5% glucose solution containing 0.05% Tween 80 as a dispersion medium.

(2) Evaluation of Particle Forming

Using various test compounds instead of Compound 4-11, with particles prepared by the same method as Formulation Example 3, the mean particle diameter and particle distribution at 30 minutes, 24 hours and 7 days after preparation were measured and evaluated in a similar manner with the above (1).
<Result>

The following shows mean particle diameter (Dv) and particle distribution (PDI) of particles in each Formulation Example stored at 5° C. for 30 minutes.

TABLE 4

| 30 min. after preparation | Dv (mm) | PDI | |
|---|---|---|---|
| Formulation Example 4 (Compound 4) | 1.529 | 2.4 | |
| Formulation Example 5 (Compound 4-1) | 1.225 | 2.3 | |
| Formulation Example 6 (Compound 4-2) | 1.699 | 2.8 | |
| Formulation Example 7 (Compound 4-3) | 1.364 | 2.3 | |
| Formulation Example 8 (Compound 4-9) | 1.279 | 2.3 | |
| Formulation Example 9 (Compound 10) | 1.357 | 2.2 | |
| Formulation Example 10 (Compound 17) | 1.928 | 3.2 | |
| Formulation Example 11 (Compound 17-1) | 1.616 | 2.6 | |
| Formulation Example 12 (Compound 17-3) | 1.753 | 2.7 | |
| Formulation Example 13 (Compound 17-4) | 2.216 | 3.6 | |
| Formulation Example 14 (Compound 19) | 1.494 | 2.4 | |
| Formulation Example 15 (Compound 19-6) | 1.508 | 2.4 | |
| Formulation Example 16 (Compound 20-1) | 1.788 | 3 | |
| Formulation Example 17 (Compound 20-2) | 2.282 | 3.4 | |
| Reference Formulation Example 1 (Reference Example 3) | — | — | |
| Reference Formulation Example 2 (Reference Example 4) | 1.865 | 2.7 | (7 days after preparation: 377.3) |
| Reference Formulation Example 3 (Reference Example 5) | 5.438 | 9.1 | |
| Reference Formulation Example 4 (Reference Example 6) | 20.061 | 50 | |

As described above, particles in Formulation Examples 4 to 17 prepared with the compound of the present invention have targeted mean particle diameter of 0.5-3 μm and 4 or less of PDI value at 30 minutes, and also 7 days after preparation.

Therefore, the compound of the present invention forms a particle which has appropriate size for intra-articulation injection and is very uniform and stable with time.

On the other hand, as well as the compound of the present invention, even when the particles were prepared with the compound of which active |form| is Compound A, for example in Reference Formulation Example 1, the compound prepared in Reference Example 3 did not form a particle since the compound was dissolved in a dispersion medium. In addition, in Reference Formulation Examples 3 and 4, the mean particle diameter far exceeded the targeted value at 30 minutes after preparation and the variation of particle distribution was large. Further, in Reference Formulation Example 2, although the compound formed particles with a targeted particle size at 30 minutes after preparation, the particle diameter increased with time and its PDI value was 377.3 at 7 days after preparation, that is, it formed unstable particles with large variation of particle distribution.

(3) In Vitro Hydrolysis Test

The particles were retained inside articular cavity after intra-articular administration. The sustained period of active form inside articular cavity changes depending on hydrolysis period of a test compound. Therefore, the hydrolysis period of a test compound was evaluated and set as an indicator of sustained release of the active form.
<Experimental Method>

Various test compounds were dissolved in dimethylsulfoxide, so that the concentration of the solution calculated in Compound A becomes 0.5 mg/mL. The solution (10 μL) was added to 0.5 mL of rabbit plasma and incubated at 37° C. in water bath. 50 μL of the solution was sampled 0, 1, 3, 8, 24, 30, 48 and 72 minutes after the incubation and the concentration of Compound A in sample was determined.
<Determination Method of Compound A>

After 50 μL of the solution was sampled in a polyethylene tube, 10 μL of deuterium-labeled Compound A as internal standard and 2 mL of acetonitrile were added, followed by stirring. After centrifugation, 100 μL of the supernatant was sampled in a polyethylene tube and 900 μL of acetonitrile was added thereto, followed by stirring. After filtration, the supernatant was measured by LC/MS/MS and the 50% hydrolysis time was calculated.
<LC/MS/MS>

TABLE 5

| LC Test Condition | | | | | | |
|---|---|---|---|---|---|---|
| Column | YMC-Pack MB-ODS, 150 × 2.1 mm I.D., S-5 μm, 12 nm | | | | | |
| Column temperature | Room Temperature | | | | | |
| Mobile phase | A: 0.1% Acetic acid    B: $CH_3CN$ | | | | | |
| Gradient time table | Time (min.) | 0 | 3 | 7 | 7.01 | 10 |
| | A % | 80 | 10 | 10 | 80 | 80 |
| | B % | 20 | 90 | 90 | 20 | 20 |
| Flow rate | 0.2 mL/min | | | | | |

TABLE 6

| MS/MS Condition | | | | |
|---|---|---|---|---|
| Ion Source | | ESI | | |
| Scan type | | MRM | | |
| Polarity | | Negative | | |
| Temperature | | 600° C. | | |
| Resolution Q1 | | unit | | |
| Resolution Q3 | | unit | | |
| Scan Time | Compound A | 200 msec | | |
| | IS | 200 msec | | |
| Monitor ion | | Precursor | Product | |
| | Compound A | m/z 397.0 | → | m/z 361.0 |
| | IS | m/z 402.0 | → | m/z 366.0 |
| Collision Gas | | 4 | | |
| Curtain Gas | | 20 psi | | |
| Ion Source Gas 1 | | 40 psi | | |
| Ion Source Gas 2 | | 70 psi | | |
| Ion Spray Voltage | | −4500 V | | |
| Declustering Potential | | −55 V | | |
| Entrance Potential | | −10 V | | |
| Collision Energy | | −22 V | | |
| Collision Cell Exit Energy | | −3 V | | |
| Interface Heater | | off | | |

<Result>

Time of 50% hydrolysis of the compound of the present invention, for example Compound 4-1, Compound 4-11, Compound 6-4 and Compound 19, was as very long as 10.6, 7.3, 7.8 and 26.2 days respectively. On the other hand, as well as the compound of the present invention, even in case of the compound of which the active |form| is Compound A, time of 50% hydrolysis of methyl(5Z)-7-{(1R,2R,3R,5R)-5-chloro-2-[(1E,4S)-4-(1-ethylchlorobutyl)-4-hydroxy-1-butenyl]-3-hydroxycyclopentyl}-5-heptenoate (the compound disclosed in Example 16 of EP 860430A) was as very short as 0.0045 day (6.5 minutes), that is, the compound was hydrolyzed in a very short time.

Thus, it is demonstrated that the compound of the present invention releases its active form inside articular cavity in a sustained manner, (4) In Vivo Pharmacokinetic Evaluation After a formulation was injected inside articular cavity, mean residence time (MRT) of active form was evaluated as an indicator to select a compound retained inside articular cavity in a sustained manner.

<Preparation of Drug Solution>

The compound of the present invention was weighed in a test tube so that the amount calculated in Compound A becomes 4.80 mg. Ethanol (0.15 mL) was added thereto and the obtained solution was added by portions to 5% aqueous glucose solution containing 0.05% Tween 80 with stirring. Further, the solution was diluted to ten times with 5% aqueous glucose solution containing 0.05% Tween 80 to prepare an administering drug solution so that that its concentration becomes 0.16 mg/mL calculated in Compound A.

<Experimental Method>

A rabbit was retained in a positioner and a drug solution was administered into an articulation of right knee at a dose of 0.228 mg/kg calculated in Compound A. With a syringe treated with heparin, 0.6 mL of blood was periodically collected from auricular vein. The collected blood was added to BIOBIK from which solvent was removed with sodium fluoride beforehand and shaked, followed by cooling with ice right after it. The concentration of sodium fluoride was adjusted to become 10 mM when whole blood is added. The concentration of Compound A in an obtained sample was measured and mean residence time (MRT) was calculated. When the amount of test compound transferred into blood is small, MRT of the active form in blood reflects the one in articular cavity. The amount of the compound of the present invention transferred into blood is as small as 2% or less.

<Result>

For example, mean residence time of Compound 4-1, Compound 4-11 and Compound 19 was as very long as 3.1, 3.1 and 2.2 days respectively.

Therefore, it is demonstrated that the compound of the present invention is retained inside articular cavity in a sustained manner.

Biological Examples

According to the following experiments, it is proved that the compound of the present invention has cartilage regeneration action and high safety by intra-articulation administration.

(1) Evaluation of Cartilage Tissue Score in Knee Cartilage Defect Model

<Preparation of Model Animal>

Knee cartilage defect model was prepared by the following method. Female Japanese white domestic rabbit (2.5-3.5 kg) was anesthetized by the administration of sodium pentobarbital (30 mg/kg) through ear vein. The hair around knee articulations of both hind legs was removed and disinfected with iodine tincture. After the incision of the skin of an inert right hind leg, the boundary between patella ligament and articular capsule was incised in dorsal position. Patella was dislocated outward to expose trochlea femoris largely and medial condyle of femur was drilled with a dental drill to prepare small hole (diameter: 4 mm, depth: about 2 mm). The surgical incision was sutured and the surgical site was disinfected with iodine tincture. Femur of a left knee or both knees of pseudo-operation group was only exposed by the same operation without preparing small hole. To avoid infection disease, 100,000 units of benzylpenicilline procaine/125 mg titers of dihydrostreptomycin sulfate/I mg of procaine hydrochloride per rabbit was administered in gluteal muscle.

<Administration of Test Compound>

A test compound (12-200 µg/knee, calculated in Compound A which is active form of test compounds) and its medium (5% glucose solution containing 0.05% Tween 80) were administered inside articular cavity of right knee of rabbit at bi-weekly intervals, 6 times for total, and from a week after operation. The medium was administered to a left knee or both knees of pseudo-operation group by the same operation.

<Sampling and Preparation of Pathological Specimen>

Blood was collected from left auricular vein before the third administration which is 5 weeks after operation, and 1, 2, 4 hours, 1, 2, 4, 7, 9, 11 and 14 days after administration. Blood was collected with a 1 mL syringe with a needle of 26 G treated with heparin beforehand (about 10 units/mL) and the collected blood was centrifuged at 4° C. 13,500 g for 5 minutes. The obtained supernatant (plasma) was stored at −80° C. and provided for the measurement of blood concentration of Compound A.

The rabbit was anesthetized by the administration of sodium pentobarbital (30 mg/kg) through car vein at 12 weeks after the operation, bled to sacrifice and the distal femur was sampled. After fixing the sample with 10% neutral buffered formalin for five days, it was degreased and dehydrated with an aqueous ethanol solution, and decalcified with dipping in ethylenediamine tetracetic acid solution (10 w/v %). The decalcified sample was embedded in paraffin and the continuous sections of 4 μm were dyed with hematoxylin-eosin solution or safranine 0-fast green solution.

<Histopathological Evaluation>

Femur specimen was observed with an optical microscope and histopathological evaluation was conducted. The histopathological evaluation was comprised of 4 items which are Cell morphology and Matrix staining (0 point: Hyaline cartilage, 2 points: Mostly hyaline cartilage, 4 points: Moderately hyaline cartilage, 6 points: Partly hyaline cartilage, 8 points: Fibrous), Surface regularity (0 point: Smooth, 1 point: Moderate, 2 points: Irregular, 3 points: Severely irregular), Filling of defect (0 point: 75-100%, 1 point: 50-75%, 2 points: 25-50%, 3 points: 0-25%, 4 points: 0%) and Reconstitution of subchondral bone and osseous connection (0 point: Yes, 1 point: Almost, 2 points: Partly, 3 points: Not close). The total score was set as cartilage tissue score indicating the defect degree of knee cartilage.

<Result>

Figure 2:
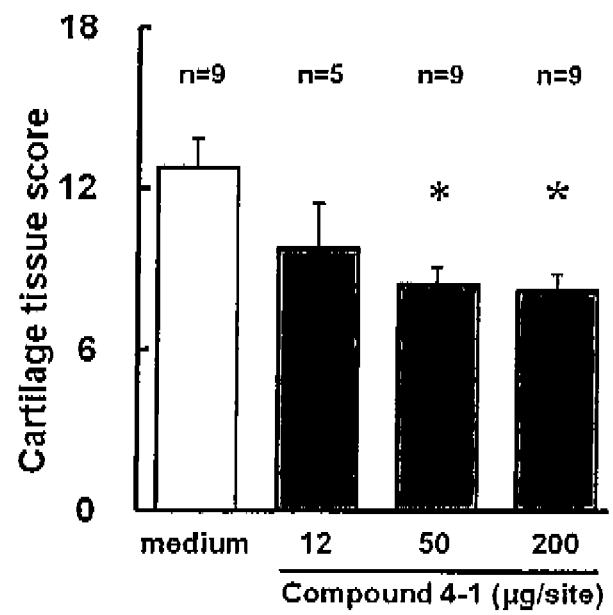
FIG. 2 shows the action of Compound 4-1 in knee cartilage defect model (*p<0.05 vs vehicle: Steel test).
Figure 3:
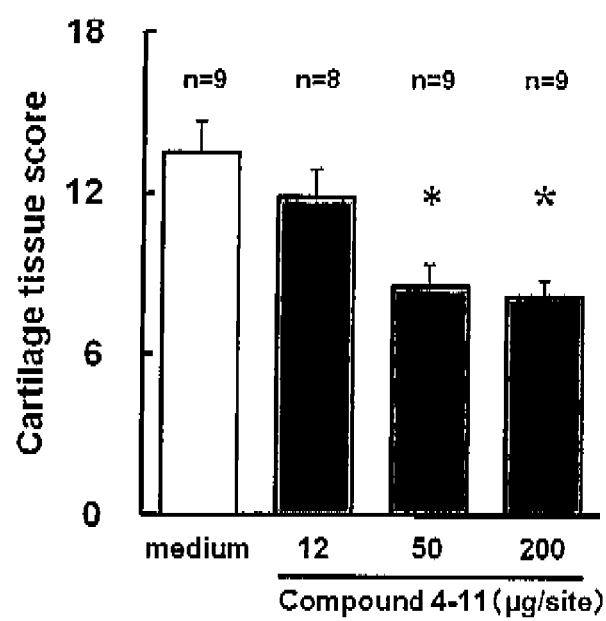
FIG. 3 shows the action of Compound 4-11 in knee cartilage defect model (*p<0.05 vs vehicle: Steel test).

The results of administration of the compounds of the present invention, for example Compound 19, Compound 4-1 and Compound 4-11 were showed in FIGS. 1, 2 and 3. Compound 19, Compound 4-1 and Compound 4-11 significantly improved cartilage tissue score.

From these results, it is proved that the compound of the present invention is effective as an agent for cartilage disorder.

As described in Table 7, when Compound 19, Compound 4-1 and Compound 4-11 were administered into articular cavity at an effective dose (50 μg), the maximum blood concentrations of Compound A were 89 pg/mL, 47 pg/mL and 82 pg/ml, respectively.

TABLE 7

|  |  | Dose of a test compound | |
|---|---|---|---|
|  |  | 50 μg | 200 μg |
| Maximum blood concentration of Compound A (pg/mL) | Compound 19 | 89 ± 51 | 237 ± 55 |
|  | Compound 4-1 | 47 ± 5 | 179 ± 120 |
|  | Compound 4-11 | 82 ± 22 | 182 ± 66 |

By using above data, the safety for the circulatory action of the compound of the present invention was evaluated with a following experiment, (2) Measurement of Blood Pressure and Heart Rate of Normal Rabbit Compound A acts on circulatory system and affects on blood pressure and heart rate. In the present experiment, the blood concentration of Compound A affecting on blood pressure and heart rate was measured and compared with the blood concentration exhibiting the cartilage regeneration action in Biological Example 1 to evaluate the safety of the compound of the present invention for its circulatory action, <Measurement Method>

Blood pressure and heart rate were measured by the following method using female Japanese white domestic rabbit. An animal was retained in dorsal position on an operation table on a measurement day. After the hair of right femur area was removed, a local anesthetic was given by administering an appropriate amount of lidocaine injection. The skin and muscle was incised to expose femur artery and vein, and a catheter (manufactured by Atom Medical Corporation) filled with saline containing heparin (about 10 units/mL) beforehand was placed in the right femur artery.

After retaining the rabbit in a rabbit blood sampling box (manufactured by NATSUME SEISAKUSHO CO LTD.), the catheter was connected to a pressure transducer (DX-100: manufactured by NIHON KOHDEN CORPORATION) to measure blood pressure with a strain pressure amplifier (AP-641G: manufactured by NIHON KOHDEN CORPORATION) and heart rate with an instantaneous heart rate counter (AT-601G: manufactured by NIHON KOHDEN CORPORATION). Blood pressure and waveform of heartbeat were recorded by a recorder (WR3701: manufactured by Graphtech Corporation). Measurement was conducted under awake condition after confirming blood pressure and heart rate became stable.

Compound A was administered cumulatively through right auricular vein with a syringe pump (manufactured by TERUMO CORPORATION) at 0 (medium: saline), 100, 300 and 1000 ng/kg/min (administration volume: 1 mL/kg/h). Each dose was administered for more than 60 minutes and blood was collected from left auricular vein 60 minutes after the administration started. Blood was collected with a 1 mL syringe with a needle of 260 treated with heparin (about 10 units/mL) beforehand. The collected blood was centrifuged at 4° C. 13,500 g for 5 minutes and the obtained supernatant (plasma) was stored at 80° C. to be provided for the measurement of blood concentration of Compound A.

Increase or decrease ratio of mean blood pressure and heart rate at 5, 10, 15, 20, 30, 40, 50 and 60 minutes after the administration started were calculated based on the values of pre-administration of each subject. Maximum change of blood pressure and heart rate between before and after the administration of Test Compounds was evaluated.

<Result>

Figure 4:
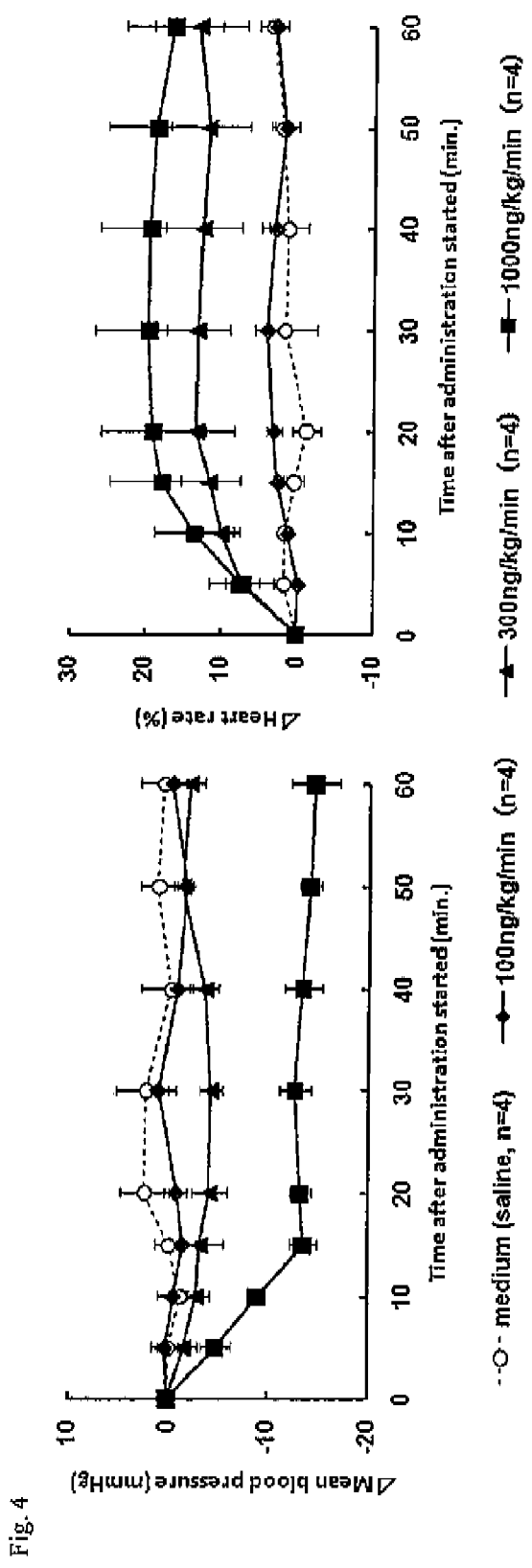
FIG. 4 shows the effect of (5Z)-7-{(1R,2R,3R,5R)-5-chloro-2-[(1E,4S)-4-(1-ethylchlorobutyl)-4-hydroxy-1-butenyl]-3-hydroxycyclopentyl}-5-heptenoic acid (The compound described in Example 17 of the EP Patent publication 860430 (it is hereafter described as the compound A)) on blood pressure (A) and heart rate (B).
Figure 5:
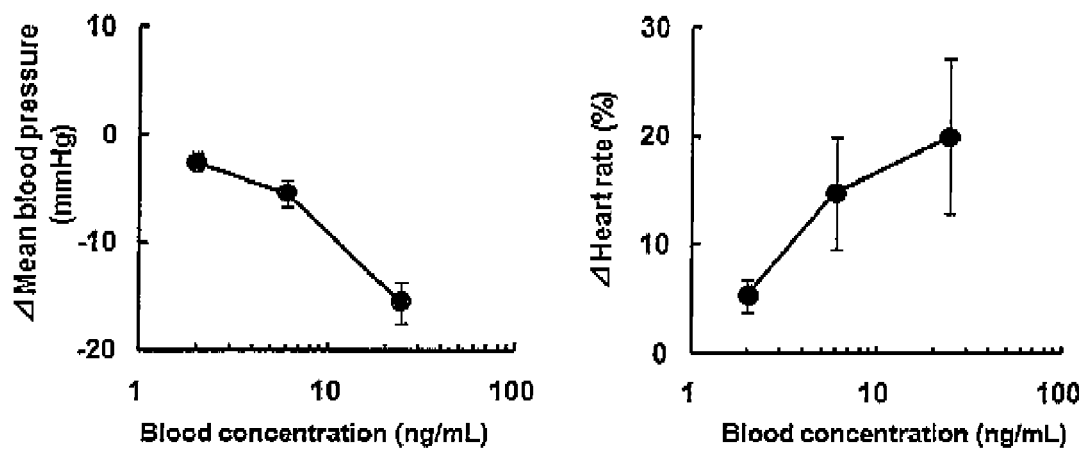
FIG. 5 shows blood pressure (A) and heart rate (B) at a blood concentration of the compound A at 60 minutes after the administration.

Results were showed in FIG. 4 and FIG. 5.

Decrease of blood pressure by the administration of medium was 3 mmHg at maximum. Compound A hardly affected on blood pressure at the administration rates of 100 and 300 ng/kg/min and the decrease of blood pressure was 5 mmHg at maximum. Further, Compound A decreased blood pressure by 16 mmHg at the administration rate of 1000 ng/kg/min.

Increase of heart rate by the administration of medium was 4% at maximum. Compound A hardly affected on heart rate at the administration rate of 100 ng/kg/min and the increase was about 5% at maximum. Further, Compound A increased heart rate by 15% and 20% at the administration rate of 300 and 1000 ng/kg/min respectively.

In addition, the blood concentration of Compound A at 60 minutes after administration started was 2.0, 5.9 or 24.3 ng/ml, respectively by the continuous intravenous administration at the administration rate of 100, 300 or 1000 ng/kg/min.

From the above, it is proved that Compound A does not affect heart rate at the blood concentration of 2.0 ng/mL or less and does not affect blood pressure at the blood concentration of 5.9 ng/mL or less.

On the other hand, as measured in Biological Example (1), the maximum blood concentration of Compound A was 89 pg/mL, 47 pg/mL and 82 pg/mL respectively when Compound 19, Compound 4-1 and Compound 4-11 was administered to inside articular cavity at the effective dose (50 μg).

From these results, it is proved that Compound 19, Compound 4-1 and Compound 4-11 hardly affects on circulatory system at the maximum dose of Compound A which exhibits the efficacy on the knee cartilage defect model.

From the result of Biological Examples (1) and (2), the compound of the present invention has cartilage regeneration action and high safety for circulatory system by intra-articular administration.

Formulation Example

In 7.2 mL of ethanol (63 mg/mL, calculated in Compound A), 879.41 mg of Compound 4-1 was weighed and dissolved.

The whole compound solution was added by portions to 172.8 mL of 10% aqueous maltose solution containing 0.104% polysorbate 80 under stirring with homomixer to prepare suspension (2.34 mg/mL, calculated in Compound A). After the suspension was filled into a vial, it was lyophilized by a known method to obtain a vial containing 2.81 mg of Compound A as the active form.

INDUSTRIAL APPLICABILITY

The compound of the present invention is injectable into articular cavity which is a part affected by diseases to improve cartilage disorder and can exhibit efficacy in a sustained manner by being retained in articular cavity. Therefore, since the compound of the present invention has an excellent cartilage regeneration action and does not develop circulatory side effect at the blood concentration exhibiting cartilage regeneration action, it is useful as a treating agent for cartilage disorder such as cartilage injury, articular disk injury, menisci injury, osteochondral defect, arthrosis deformation and the like.

Further, since a suspension prepared with the compound of the present invention can be injected without incising an affected part, it reduces a patient burden and is very useful as medicine.

The invention claimed is:
1. A compound represented by a formula (I):

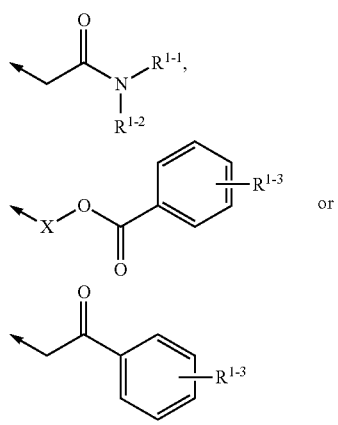

(I)

wherein $R^1$ is C10-22 alkyl, C10-22 alkenyl and C10-22 alkynyl,

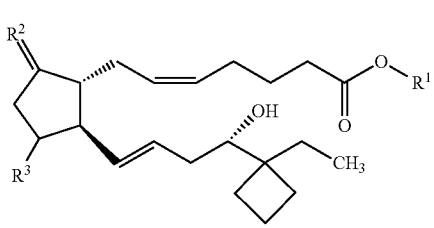

wherein an arrow of each group represents a bond position,
X is C2-4 alkylene;
$R^{1-1}$ is C10-20 alkyl optionally substituted by one phenyl, C10-20 alkenyl optionally substituted by one phenyl, C10-20 alkynyl optionally substituted by one phenyl, phenyl substituted by C10-20 alkyl, phenyl substituted by C10-20 alkenyl or phenyl substituted by C10-20 alkynyl;
$R^{1-2}$ is C1-3 alkyl or phenyl;
$R^{1-3}$ is C10-20 alkyl, C10-20 alkenyl, C10-20 alkynyl, C10-20 alkoxy, C10-20 alkenyloxy or C10-20 alkynyloxy;
$R^2$ is a hydrogen atom, hydroxy, oxo or a halogen atom;
$R^3$ is a hydrogen atom or hydroxy;

----- represents a single bond or double bond;

$\mathrm{``}^{\mathrm{``}}$ represents binding to the opposite side of the sheet (namely α-configuration), ◢ represents binding to the front side of the sheet (namely β-configuration), ◢ represents that it is α-configuration, β-configuration or a mixture thereof at arbitrary ratio,
a solvate thereof or a cyclodextrin clathrate thereof.

2. The compound according to claim 1,
wherein $R^1$ is C12-22 alkenyl, C12-22 alkynyl or

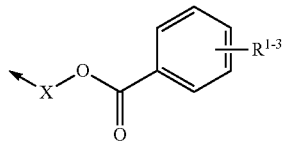

wherein all symbols in formula have the same meanings as described in claim 1.

3. The compound according to claim 1, which is selected from a group consisting of 3-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}propyl 3-(pentadecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 3-(pentadecyloxy)benzoate, 4-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}butyl 3-(pentadecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 3-(dodecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 3-(tetradecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 3-(hexadecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 3-(octadecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 2-(pentadecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 4-(decyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 4-(dodecyloxy)benzoate, 2-{[(5Z)-7-{(1R,2R,3R,5R)-5- chloro-2-[(1E,4S)-4-(1-ethylcyclobutyl)-4-hydroxy-1-buten-1-yl]-3-hydroxycyclopentyl}-5-heptenoyl]oxy}ethyl 4-(tetradecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 4-(pentadecyloxy)benzoate, 3-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}propyl 4-(pentadecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 4-(hexadecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 4-(octadecyloxy)benzoate, (2R)-1-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}-2-propyl 4-(tetradecyloxy)benzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 3-hexadecylbenzoate, 3-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}propyl 3-hexadecylbenzoate, 4-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}butyl 3-hexadecylbenzoate, 2-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}ethyl 4-hexadecylbenzoate, 3-{[(5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoyl]oxy}propyl 4-hexadecylbenzoate, 2-[methyl(4-pentadecylphenyl)amino]-2-oxoethyl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-[metyl(15-phenylpentadecyl)amino]-2-oxoethyl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-[methyl(tetradecyl)amino]-2-oxoethyl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-[hexadecyl(methyl)amino]-2-oxoethyl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-[methyl(octadecyl)amino]-2-oxoethyl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-[icosyl(methyl)amino]-2-oxoethyl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-[ethyl(octadecyl)amino]-2-oxoethyl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-[octadecyl(phenyl)amino]-2-oxoethyl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-octadecyn-1-yl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-pentadecyn-1-yl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-heptadecyn-1-yl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-nonadecyn-1-yl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, 2-henicosyn-1-yl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, (2E)-2-hexadecen-1-yl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, (2E)-2-octadecen-1-yl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, (2E)-2-icosen-1-yl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, (2Z)-2-octadecen-1-yl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, undecyl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, octadecyl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate, and 2-oxo-2-[2-(pentadecyloxy)phenyl]ethyl (5Z)-7-{(1R,2R,3R,5R)-5-chloro-2-[(1E,4S)-4-(1-ethylcyclobutyl)-4-hydroxy-1-buten-1-yl]-3-hydroxycyclopentyl}-5-heptenoate.

4. A particle formed by a compound represented by formula (I) as defined in claim 1, a solvate thereof or a cyclodextrin clathrate thereof.

5. The particle according to claim 4, wherein the mean particle diameter is 0.5 to 5 μm.

6. A suspension which comprises a compound represented by formula (I) as defined in claim 1, a solvate thereof or a cyclodextrin clathrate thereof, and as a dispersion medium, one or more kind selected from glucose solution, maltose solution, sucrose solution, lactose solution, trehalose solution, mannitol solution, maltitol solution, xylitol solution, dextran, distilled water for injection and saline, and also may comprise surfactant.

7. An agent for the prevention and/or treatment of cartilage disorder, comprising a compound represented by formula (I) as defined in claim 1, a solvate thereof or a cyclodextrin clathrate thereof.

8. A method of the prevention and/or treatment of cartilage disorder, which comprises administering a compound represented by formula (I) as defined in claim 1, a solvate thereof or a cyclodextrin clathrate thereof to a mammal.

9. A compound represented by formula (I) as defined in claim 1, a solvate thereof or a cyclodextrin clathrate thereof for preventing and/or treating cartilage disorder.

\* \* \* \* \*